US008501907B2

(12) United States Patent
Jordan et al.

(10) Patent No.: US 8,501,907 B2
(45) Date of Patent: Aug. 6, 2013

(54) IMMUNOGLOBULIN CLEAVAGE FRAGMENTS AS DISEASE INDICATORS AND COMPOSITIONS FOR DETECTING AND BINDING SUCH

(75) Inventors: Robert Jordan, Thorton, PA (US); David Knight, Berwyn, PA (US); Randall Brezski, Spring House, PA (US); Mary Ryan, Spring House, PA (US); Diane Petrone, Chesterbrook, PA (US)

(73) Assignee: Janssen Biotech, Inc., Horsham, PA (US)

( * ) Notice: Subject to any disclaimer, the term of this patent is extended or adjusted under 35 U.S.C. 154(b) by 84 days.

(21) Appl. No.: 12/950,240

(22) Filed: Nov. 19, 2010

(65) Prior Publication Data
US 2011/0076264 A1 Mar. 31, 2011

Related U.S. Application Data

(63) Continuation-in-part of application No. 12/185,333, filed on Aug. 4, 2008, now abandoned.

(60) Provisional application No. 60/955,162, filed on Aug. 10, 2007.

(51) Int. Cl.
*A61K 38/00* (2006.01)
*C07K 14/00* (2006.01)

(52) U.S. Cl.
USPC .......................................... 530/300; 530/327

(58) Field of Classification Search
None
See application file for complete search history.

(56) References Cited

U.S. PATENT DOCUMENTS

| | | | |
|---|---|---|---|
| 6,838,254 B1 | 1/2005 | Hamers et al. | |
| 7,129,331 B2 | 10/2006 | Pestka | |
| 7,666,582 B2 | 2/2010 | Pawel-Rammingen et al. | |
| 2009/0155280 A1 | 6/2009 | Jordan et al. | |
| 2010/0260751 A1 | 10/2010 | Raju et al. | |

OTHER PUBLICATIONS

Burgess et al ., J Cell Biol. 111:2129-2138, 1990.*
Ngo et al, in The Protein Folding Problem and Tertiary Structure Prediction, 1994. (ed.), Birkhauser, Boston, MA, pp. 433 and 492-495.*
Wang et al. JBC, 2001 276:49213-49220.*
Pellequer et al ., Method Enzymol, 1991, v. 203, pp. 176-201.*
Schmidt et al., "A synthetic peptide approach for elucidating the points of natural auto-antibody reactivity to proteolytic fragments of human IgG", Biopolymers, New York, NY, vol. 88, No. 4, p. 556, XP09142664 (Jan. 1, 2007).
Centocor Ortho Biotech Inc., Supplementary European Search Report for EP08782610 dated Jan. 17, 2011.
Brezski et al., "Cleavage of IgGs by proteases associated with invasive diseases: an evasion tactic against host immunity?", Mabs., vol. 2, No. 3, pp. 212-220 May 2010.
Brezski et al., Human anti-IgG1 hinge autoantibodies reconstitute the effector functions of proteoltically inactivated IgGs., Proc. Natl. Acad. Sci. USA, vol. 106, No. 42, pp. 17864-17869 Oct. 2009.
Brezski et al., "Human antiIgGl hinge autoantibodies reconstitute the effector functions of proteolytically inactivated IgGs.", Journal of Immunology, vol. 181, No. 5, pp. 3183-3192 Sep. 2008.
Nandakumar et al., "Blocking of experimental arthritis by cleavage of IgG antibodies in vivo", Arthritis Rheum., vol. 56, No. 10, pp. 3253-3260, Oct. 2007.
Eriksson et al., "Cleavage of antigen-bound immunoglobulin G by SpeB contributes to streptococcal persistence in opsonizing blood", Infect Immun., vol. 71, No. 1, pp. 211-217, Jan. 2003.
Bianchi et al., "Universal influenza B vaccine based on the maturational cleavage site of the hemaggluthinin precursor", Journal Virol., vol. 79, No. 12, pp. 7380-7388, Jun. 2005.
Knight et al, "The Immunogenicity of the 7E3 Murine Monocolona FAB Antibody Fragment Variable Region is Dramatically Reducedin Humans By substitution of Human for Murine Constact Regions", Molecular Immunology, vol. 32; pp. 1271-1281, (1995).
Nasu et al. 1980, "Characterization of anti-F(ab')$^2$ antibodies in SLE patients evidence for cross-reacting autoanti-idiotypic antibodies", Clinical Immunology and Immunopathology, vol. 25., No. 1, pp. 80-90 (1982).
Persselin and Stevens, "Anti-Fab antibodies in humans: Predominance of minor immunoglobulin G subclasses in rheumatoid arthritis", J. Clinical Investigation, vol. 76, pp. 723-730, (1985).
Terness et al., "The Natural Human IgG Anti-F(ab')$_2$ Antibody Recognizes a Conformational IgG1 Hinge Epitope[1]", Journal of Immunology 154, pp. 6446-6452 (1995).
Fick et al., "IgG Proteolytic Activity of *Pseudomonas aeruginosa* in Cystic Fibrosis", Journal of Infectious Diseases, vol. 151, No. 4, pp. 589-598 (1985).
Goldberg et al., "F(ab')$_2$-like Fragments from Severely Burned Patients provide a New Serum Immunoglobin Component", Nature, vol. 228, pp. 160-162 (1970).
Marion Waller, "IgG Hydrolysis in Abscesses, I. A Study of the IgG in Human Abscess Fluid", Immunology, vol. 26, pp. 725-733 (1974).
Eckle et al., "Detection of Granulocyte Elastase Specific IgG Split Products in Rheumatoid Synovial Fluid", Avd. Exp. Med. Biol., 204: pp. 531-534 (1988).
Gearing AJH et al., "Selective cleavage of human IgG by the matrix metalloproteinases, atrilysin and stromelysin", Immunology Letters, vol. 81, No. 1, pp. 41-48 (2002).
Vincents et al., "Enzymatic characterization of the streptococcal endopeptidase, IdeS, reveals that it is a cysteine protease with strict specificity for IgG cleavage due to exosite binding", Biochemistry 43: pp. 15540-15549 (2004).

(Continued)

*Primary Examiner* — Michail Belyavskyi
(74) *Attorney, Agent, or Firm* — Kenneth J. Dow

(57) ABSTRACT

The invention relates to antibody compositions and use of the composition to detect disease processes associated with elaboration of proteases. The reagents are directed to assessing an IgG breakdown product that is the result of such proteolytic cleavage. The invention further relates to the use of a therapeutic immunospecific for IgG protease cleavage products to restore effector function to antibody compositions that are subject to protease cleavage.

5 Claims, 16 Drawing Sheets

(56) References Cited

OTHER PUBLICATIONS

Barrett, et al, Handbook of Proteolytic Enzymes, vol. 1, pp. 43-48; Elsevier, Amsterdam (2004).
Barrett, et al, Handbook of Proteolytic Enzymes, vol. 1, pp. 472-480; Elsevier, Amsterdam (2004).
Barrett, et al, Handbook of Proteolytic Enzymes, vol. 1, pp. 480-483; Amsterdam (2004).
Barrett, et al, Handbook of Proteolytic Enzymes, vol. 1, pp. 512-523; Elsevier, Amsterdam (2004).
Barrett, et al, Handbook of Proteolytic Enzymes, vol. 1, pp. 532-537; Elsevier, Amsterdam (2004).
Barrett, et al, Handbook of Proteolytic Enzymes, vol. 1, pp. 540-544; Elsevier, Amsterdam (2004).
Barrett et al., Handbook of Proteolytic Enzymes, vol. 2, pp. 1079-1083; Elsevier, Amsterdam (2004).
Barrett et al., Handbook of Proteolytic Enzymes, vol. 2, pp. 1104-1107; Elsevier, Amsterdam (2004).
Barrett et al., Handbook of Proteolytic Enzymes, vol. 2, pp. 1448-1451; Elsevier, Amsterdam (2004).
Barrett et al., Handbook of Proteolytic Enzymes, vol. 2, pp. 1489-1492; Elsevier, Amsterdam (2004).
Barrett et al., Handbook of Proteolytic Enzymes, vol. 2, pp. 1504-1507; Elsevier, Amsterdam (2004).
Barrett et al., Handbook of Proteolytic Enzymes, vol. 2, pp. 1517-1523; Elsevier, Amsterdam (2004).
Barrett et al., Handbook of Proteolytic Enzymes, vol. 2, pp. 1524-1525; Elsevier, Amsterdam (2004).
Barrett et al., Handbook of Proteolytic Enzymes, vol. 2, pp. 1526-1530; Elsevier, Amsterdam (2004).
Barrett et al., Handbook of Proteolytic Enzymes, vol. 2, pp. 1531-1534; Elsevier, Amsterdam (2004).
Barrett et al., Handbook of Proteolytic Enzymes, vol. 2, pp. 1577-1579; Elsevier, Amsterdam (2004).
Barrett et al., Handbook of Proteolytic Enzymes, vol. 2, pp. 1692-1695; Elsevier, Amsterdam (2004).
Powers, JC., "Proteolytic Enzymes and Disease Treatment", Modification of Proteins: Food, Nutritional, and Pharmacological Aspects, Advances in Chemistry Series 198 ACS, Washington, D.C. pp. 347-367, Feeney and Whitaker (eds.) (1982).
Tchetverikov et al., "MMP Profile in paired serum and synovial fluid samples of patents with rheumatoid arthritis", Ann. Rheum. Dis, vol. 63, pp. 881-883, (2004).
Sun et al., "Plasminogen is a critical host pathogenicity factor for group A streptococcal infection", Science, vol. 305, pp. 1283-1286 (2004).
Welschof et al., "The Antigen Binding Domain of Non-idiotypic Human anti-F(ab")$^2$ Autoantibodies: Study of their interation with IgG Hinge Region Epitopes", Human Immunology, vol. 60, No. 4, pp. 282-290 (1999).
Welschof et al., "The antigen-binding domain of a human IgG-anti F9ab')$^2$ autoantibody", Proc. Nat. Acad. Sci (USA), vol. 94, pp. 1902-1907 (1997).
Yano et al., "Natural antibodies against the immunoglobulin F(ab')$^2$ from the circulation", Eur. J. Immunol. vol. 25, No. 11, pp. 3128-3133 (1995).
Ryan et al., "Proteolysis of purified IgGs by human and bacterial enzymes in vitro and the detection of specific proteolytic fragments of endogenous IgG in rheumatoid synovial fluid", Molecular Immunology, vol. 45, pp. 1837-1846 (2008).
Yamaguchi et al., "Proteolytic fragmentation with high specificity of mouse immunoglobulin G"", Journal of Immunological Methods, vol. 181, pp. 259-267 (1995).
Süsal et al., "Induction of Anti-F(ab)$_{2y}$ Antibodies by Buffy Coat Transfusions and Their Effect in Kidney Transplantation", Transplantation Proceedings, vol. 22, No. 4, pp. 1893-1894 (1990).
Brezski et al., "Tumor-associated and microbial proteases compromise host IgG effector functions by a single cleavage proximal to the hinge", PNAS, pp. 1-6 (2009).
Fumia et al., "Human F(ab)$_2$-containing immune complexes together with anti-hinge natural antibodies stimulate complement amplification in vitro and in vivo", Molecular Immunology, vol. 45, pp. 2951-2961 (2008).
Terness et al., "A Natural IgA-Anti-F(ab)$_{2y}$ Autoantibody Occurring in Healthy Individuals and Kidney Graft Recipients Recognizes an IgG1 Hinge Region Epitope", The American Association of Immunologists, pp. 4251-4257 (1996).
Centocor Ortho Biotech Inc., International Search Report for PCT/US10/57396 dated Jun. 9, 2011.

* cited by examiner

```
                         SEQUENCE LISTING

<160> NUMBER OF SEQ ID NOS: 16

<210> SEQ ID NO 1
<211> LENGTH: 25
<212> TYPE: PRT
<213> ORGANISM: Homo sapiens

<400> SEQUENCE: 1

Ser Cys Asp Lys Thr His Thr Cys Pro Pro Cys Pro Ala Pro Glu Leu
1               5                   10                  15

Leu Gly Gly Pro Ser Val Phe Leu Phe
            20                  25

<210> SEQ ID NO 2
<211> LENGTH: 41
<212> TYPE: PRT
<213> ORGANISM: Homo Sapiens

<400> SEQUENCE: 2

Thr Cys Asn Val Asp His Lys Pro Ser Asn Thr Lys Val Asp Lys Arg
1               5                   10                  15

Val Glu Ser Lys Tyr Gly Pro Pro Cys Pro Ser Cys Pro Ala Pro Glu
            20                  25                  30

Phe Leu Gly Gly Pro Ser Val Phe Leu
        35                  40

<210> SEQ ID NO 3
<211> LENGTH: 41
<212> TYPE: PRT
<213> ORGANISM: Homo sapiens

<400> SEQUENCE: 3

Thr Cys Asn Val Asp His Lys Pro Ser Asn Thr Lys Val Asp Lys Thr
1               5                   10                  15

Val Glu Arg Lys Cys Cys Val Glu Cys Pro Pro Cys Pro Ala Pro Pro
            20                  25                  30
```

```
Val Ala Gly Pro Ser Val Phe Leu Phe
        35                  40

<210> SEQ ID NO 4
<211> LENGTH: 40
<212> TYPE: PRT
<213> ORGANISM: Homo sapiens

<400> SEQUENCE: 4

Ser Cys Asp Thr Pro Pro Pro Cys Pro Arg Cys Pro Glu Pro Lys Ser
1               5                   10                  15

Cys Asp Thr Pro Pro Pro Cys Pro Arg Cys Pro Ala Pro Glu Leu Leu
            20                  25                  30

Gly Gly Pro Ser Val Phe Leu Phe
        35                  40

<210> SEQ ID NO 5
<211> LENGTH: 14
<212> TYPE: PRT
<213> ORGANISM: Homo sapiens

<400> SEQUENCE: 5

Ser Cys Asp Lys Thr His Thr Cys Pro Pro Cys Pro Ala Pro
1               5                   10

<210> SEQ ID NO 6
<211> LENGTH: 14
<212> TYPE: PRT
<213> ORGANISM: Homo sapiens

<400> SEQUENCE: 6

Cys Asp Lys Thr His Thr Cys Pro Pro Cys Pro Ala Pro Glu
1               5                   10

<210> SEQ ID NO 7
<211> LENGTH: 14
<212> TYPE: PRT
<213> ORGANISM: Homo sapiens

<400> SEQUENCE: 7

Thr His Thr Cys Pro Pro Cys Pro Ala Pro Glu Leu Leu Gly
1               5                   10

<210> SEQ ID NO 8
<211> LENGTH: 14
<212> TYPE: PRT
<213> ORGANISM: Homo sapiens

<400> SEQUENCE: 8

Thr Lys Val Asp Lys Lys Val Glu Pro Lys Ser Cys Asp Lys
1               5                   10

<210> SEQ ID NO 9
<211> LENGTH: 14
<212> TYPE: PRT
<213> ORGANISM: Homo sapiens

<400> SEQUENCE: 9

Lys Val Asp Lys Lys Val Glu Pro Lys Ser Cys Asp Lys Thr
1               5                   10

<210> SEQ ID NO 10
<211> LENGTH: 14
<212> TYPE: PRT
```

-continued

```
<213> ORGANISM: Homo sapiens

<400> SEQUENCE: 10

Asp Lys Thr His Thr Cys Pro Pro Cys Pro Ala Pro Glu Leu
1               5                   10

<210> SEQ ID NO 11
<211> LENGTH: 14
<212> TYPE: PRT
<213> ORGANISM: Homo sapiens

<400> SEQUENCE: 11

Val Asp Lys Lys Val Glu Pro Lys Ser Cys Asp Lys Thr His
1               5                   10

<210> SEQ ID NO 12
<211> LENGTH: 12
<212> TYPE: PRT
<213> ORGANISM: Artificial sequence
<220> FEATURE:
<223> OTHER INFORMATION: chemical analogue of human IgG1 peptide
      sequence

<400> SEQUENCE: 12

Thr Ala Pro Pro Ala Pro Ala Pro Glu Leu Leu Gly
1               5                   10

<210> SEQ ID NO 13
<211> LENGTH: 12
<212> TYPE: PRT
<213> ORGANISM: Artificial Sequence
<220> FEATURE:
<223> OTHER INFORMATION: Serine subsituted IdeS cleavage site specific
      peptide

<400> SEQUENCE: 13

Thr Ser Pro Pro Ser Pro Ala Pro Glu Leu Leu Gly
1               5                   10

<210> SEQ ID NO 14
<211> LENGTH: 12
<212> TYPE: PRT
<213> ORGANISM: Artificial sequence
<220> FEATURE:
<223> OTHER INFORMATION: Position 4 substitute human IgG1 cleavage
      fragment

<400> SEQUENCE: 14

Thr Ser Pro Pro Ser Pro Ala Pro Ala Leu Leu Gly
1               5                   10

<210> SEQ ID NO 15
<211> LENGTH: 12
<212> TYPE: PRT
<213> ORGANISM: Artificial Sequence
<220> FEATURE:
<223> OTHER INFORMATION: Position 3 and 4 substitute human IgG1 cleavage
      fragment

<400> SEQUENCE: 15

Thr Ser Pro Pro Ser Pro Ala Pro Glu Ala Leu Gly
1               5                   10

<210> SEQ ID NO 16
<211> LENGTH: 12
<212> TYPE: PRT
<213> ORGANISM: Artificial sequence
<220> FEATURE:
```

-continued

```
<223> OTHER INFORMATION: Peptide immunogen based on Strep pyrognes
      cleavage of human IgG1

<400> SEQUENCE: 16

Cys Thr Ser Pro Pro Ser Pro Ser Pro Ala Pro Glu
1               5                   10
```

IMMUNOGLOBULIN CLEAVAGE FRAGMENTS AS DISEASE INDICATORS AND COMPOSITIONS FOR DETECTING AND BINDING SUCH

CLAIM TO RIGHT OF PRIORITY

This application claims priority to U.S. patent application Ser. No. 12/185,333 filed 4 Aug. 2008, and U.S. Provisional Application No. 60/955,162, filed 10 Aug. 2007, the contents of which is incorporated herein by reference in its entirety.

BACKGROUND OF THE INVENTION

1. Field of the Invention

The invention relates to diagnostic and prognostic indicators and methods and reagents for their detection. The invention further relates to methods of monitoring the natural history of disease in a patient as well as methods for treating pathological conditions by vaccinating or administering antibodies specific for immunoglobulin cleavage sites to restore effector function of antibodies.

2. Description of the Related Art

In medicine, a biomarker is a biochemical substance that can be used to measure the progress of disease or the effects of treatment, that is, a diagnostic or prognostic indicator. One example is hemoglobin A1c which serves as a recent record of the excursion of blood glucose away from ideal levels as well as the duration of such excursions for glycemic control in diabetic patients.

Circulating immunoglobulins, and specifically those antibodies of the IgG class, are major serum proteins. It is well-known that human proteases are associated with inflammatory, proliferative, metastatic, and infectious diseases. Human proteases such as matrix metalloproteinases (MMPs) and neutrophil elastase cleave the IgGs heavy chain polypeptide at a residue unique to each protease as do bacterial proteases such as glutamyl endopeptidase (Staph. aureus) or immunoglobulin degrading enzyme of streptococcus (Strep. pyogenes). The cleavage sites in the heavy chain are clustered around the region termed the hinge domain, where the interchain disulfide linkage of the two heavy chains occurs. The region below the hinge constitutes the Fc region and comprises binding sites responsible for the effector functions of IgG. In the case of microorganisms, protease expression is a potential adjunctive virulence pathway allowing organisms to avoid opsonization (Rooijakkers et al. Microbes and Infection 7: 476-484, 2005) in so far as the proteolytic release of the Fc domain by cleavage below the hinge effectively neutralizes functions that would otherwise lead to the targeting and killing of that pathological cell. Thus, the elaboration of specific proteases may be representative of a myriad of diseases states including cancer, inflammation and infectious diseases.

That IgG degradation is enhanced in pathologic in vivo environments as evidenced by the presence of natural IgG autoantibodies that bind to the cleaved hinge domain (Knight et al., 1995; Nasu et al., 1980; Persselin and Stevens, 1985; Terness, et al. 1995 J Immunol. 154: 6446-6452). These autoantibodies also bind the Fab and F(ab')$_2$ fragments generated by several proteinases (including papain and pepsin), with particularly strong reactivity to the lower hinge domain remaining as C-terminal residues in F(ab')2 molecules (Terness et al., 1995). The detection of the actual cleavage products have been reported (Fick et al., 1985; Goldberg and Whitehouse, 1970; Waller, 1974) but a robust assay which would allow these fragments to serve as biomarkers has not been developed possibly due to the low concentrations in serum resulting from rapid clearance of the various fragments or to technical problems in detecting the fragments amidst the large amount of intact immunoglobulin in blood and tissues. A specific antibody was prepared (Eckle, et al. 1988. Adv. Exp. Med. Biol. 240: 531-534) for detection of human neutrophil elastase cleaved Fc domain detected Fc at a median concentration of 0.62 ug/ml directly in synovial fluid of rheumatoid arthritis patients but not in synovial fluid from patients with other types of joint disease.

Therefore, the ability to assess the type and amount of IgG cleavage product(s) in the bodily fluids or blood of subjects could be used as a biomarker of specific disease activity. Specific reagents and methods for such determinations would provide useful tools for diagnostic and prognostic medical assays. Further, the ability to correct loss of IgG functions in vivo due to cleavage and the ability to compensate the process of IgG cleavage in the body of subjects suffering from protease specific disease activity has not been heretofore envisioned as a therapeutic strategy.

SUMMARY OF THE INVENTION

The invention relates to reagents and use of the reagents to detect a disease process associated with elaboration of proteases, which proteases are manifestations of the disease pathology as well as agents which limit host immunological defenses. In one aspect of the invention, the reagents and use of the reagents in an assay, detect antibodies which are specific for targets related to the disease pathology. The reagents are directed to assessing an IgG breakdown product that is the result of such proteolytic cleavage.

In another embodiment of the invention, the methods of the invention are directed to detection of an IgG cleavage product which is characterized by 1) having a molecular weight which is comparable to an intact mammalian IgG under physiological conditions and 2) being separable into two fragments which comprise an antigen binding fragment and a 32 kDa fragment under denaturing but non-reducing conditions and 3) does not exhibit ADCC activity in an in vitro assay. In one aspect of the method of detecting the IgG cleavage product of the invention, a specific reagent capable of detecting the cleavage product is provided, which reagent is at least one antibody capable of binding to said cleavage product.

In another embodiment of the invention, disease specific cleavage site peptides representing the newly created C-terminal sequence of an IgG cleavage product are provided. These peptides are also useful for immunizing, panning, and selection of the anti-IgG cleavage product antibody of the invention. In one aspect, the peptide is selected from the group consisting of at least five (5) contiguous amino acids selected from the human IgG hinge region sequences of SEQ ID NO: 1, 2, 3, or 4 that are on the amino terminal side of a protease cleavage site. In one embodiment, the polypeptides are selected from those of SEQ ID NOs. 5-11 and N-terminal truncations thereof. In another aspect, a method of designing a peptide immunogen based on the proteolytic cleavage site of a human IgG molecule is provided.

In one embodiment of the invention, methods of preparation of an anti-IgG cleavage product antibody of the invention are provided including nucleic acid sequences, vectors, and host cells for the recombinant production of anti-IgG cleavage product antibodies. In another aspect of the method of manufacturing the anti-IgG cleavage product antibodies, immunized host animals are provided which animals provide an antibody of the invention. In a particular embodiment, the animal is a human and the anti-IgG cleavage product is generated by administration of a cleavage site peptide immunogen selected from the group consisting of at least five (5) contiguous amino acids selected from the human IgG hinge region sequences of SEQ ID NO: 1, 2, 3, or 4 that are on the amino terminal side of a protease cleavage site such as the sequences of SEQ ID NOs. 5-11 and N terminal truncations thereof.

In another embodiment of the invention, a kit for detection of anti-IgG cleavage product is provided comprising anti-IgG cleavage product antibodies of the invention for use in diagnosis or monitoring a disease characterized by the production of IgG cleaving proteases.

A further embodiment of the invention, is a method of administering an anti-IgG cleavage specific antibody to a patient as a method of treatment, thereby restoring effector functions to a therapeutic antibody composition which has been subjected to protease degradation. In accordance with the method, effector function is restored to the IgG cleavage product by administering the antibodies of the present invention which specifically bind to the IgG cleavage product.

In another aspect of the invention, a human suffering from a disease characterized by the elaboration of disease specific proteases, can be treated by administration of a cleavage site specific peptide immunogen selected from the group consisting of at least five (5) contiguous amino acids of the human IgG hinge region sequences of selected from SEQ ID NO: 1, 2, 3, or 4; and that are positions on the amino (N) terminal side of a protease cleavage site such as the sequences of SEQ ID NOs. 5-11 and N-terminal truncations, species homologs and chemical homologs thereof, to restore effector functions of IgG cleavage products in such patient. In a specific embodiment, the cleavage site specific peptide immunogen is represented by a peptide fragment that is N-terminal to the cleaved human IgG1 terminating with amino acid Glu233 (EU numbering), and the disease is selected from a S. aureus infection characterized by the release of glutamyl endopeptidase I (GluV8), or neutrophilic release of cathepsin G. In another embodiment, the cleavage site specific peptide immunogen is represented by a peptide fragment which is N-terminal cleaved human IgG1 terminating with amino acid Pro232 (EU numbering), and the disease is a form of human cancer characterized by the release of MMP-3 or MMP-12. In another embodiment, the cleavage site specific peptide immunogen is represented by a peptide fragment N-terminal to the IdeS of Streptococcus pyogenes cleaved human IgG1 terminating at Gly236 (EU numbering), and the disease is a Streptococcus spp infection.

In another embodiment of the invention, a kit is provided comprising anti-IgG cleavage product antibodies of the invention and instructions for use.

BRIEF DESCRIPTION OF THE SEQUENCE LISTING

Figure 1:
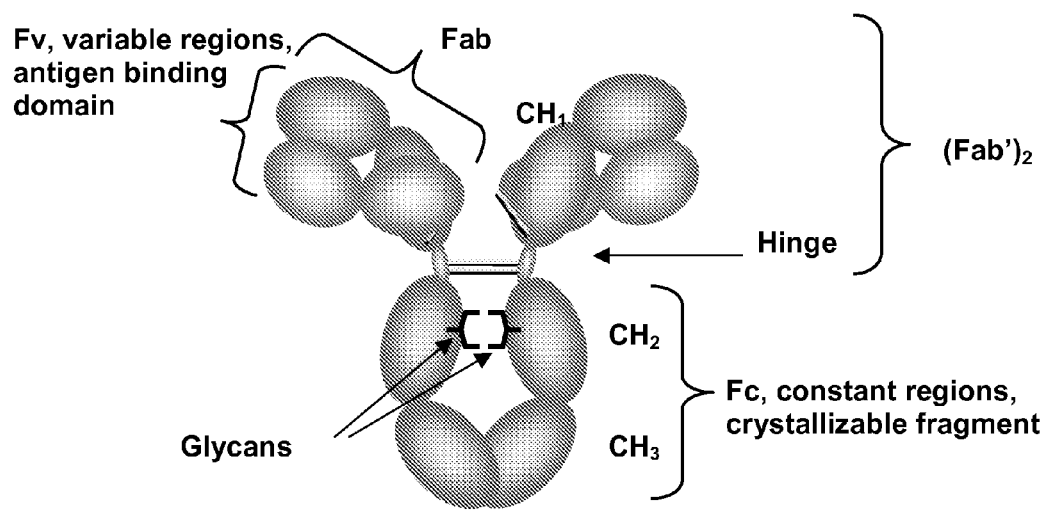
FIG. 1 depicts the various domains of a typical mammalian IgG class antibody showing their relationship to the hinge and the pepsin and papain cleavage products defined as Fab, F(ab')$_2$, and Fc.

| SEQ ID NO: | DESCRIPTION |
|---|---|
| 1 | Human IgG1 hinge region |
| 2 | Human IgG4 hinge region |
| 3 | Human IgG2 hinge region |
| 4 | Human IgG3 hinge region |
| 5 | MMP-3 and MMP12 cleavage peptide |
| 6 | Glutamyl endopeptidase 1 and Cathepsin G cleavage peptide |
| 7 | IdeS cleavage peptide |
| 8 | Plasmin cleavage peptide |
| 9 | HNE cleavage peptide |
| 10 | Pepsin and MMP-7 cleavage peptide |
| 11 | Papain cleavage peptide |
| 12 | IdeS analogue cleavage site peptide immunogen, TAPPAPAPELLG |
| 13 | IdeS analogue cleavage site peptide, TSPPSPAPELLG |
| 14 | IdeS false analogue cleavage site peptide, TSPPSPAPALLG |
| 15 | IdeS false analogue cleavage site peptide, TSPPSPAPEALG |
| 16 | Glutamyl endopeptidase cleavage site analogue peptide, CTSPPSPSPAPE |

DETAILED DESCRIPTION OF THE INVENTION

Abbreviations

Abs=antibodies, ADCC=antibody-dependent cell-mediated cytotoxicity; CDC=complement directed cytoxicity; HNE=human neutrophil elastase; IdeS=immunoglobulin degrading enzyme of *S. pyrogenes*; Ig=immunoglobulin; Mab=monoclonal antibody; MMP=matrix metalloprotease or metalloproteinase; N-terminal=amino terminal; scIgG=single cleaved IgG; SA=streptavidin; GluV8=glutamyl endopeptidase I from *Staph. aureus*.

Definitions

Antibody fragments; Fab, F(ab')$_2$, and Fc are terms describing proteolytic cleavage products of IgG antibodies which may be further dissociated by reduction of the disulfide bonds between the heavy chains (the core hinge region). Classic proteolytically generated antibody fragments, include: Fab (e.g., by papain digestion), Fab' (e.g., by pepsin digestion and partial reduction) and F(ab')$_2$ (e.g., by pepsin digestion), facb (e.g., by plasmin digestion), pFc' (e.g., by pepsin or plasmin digestion), Fd (e.g., by pepsin digestion, partial reduction and reaggregation), where reduction removes the disulfide linkage between cysteine residues forming interchain linkages (refer to FIG. 1). As the Fc fragment was described as a papain cleavage fragment and because papain cleaves human IgG1 at residue 224 (EU numbering), which is N-terminal to the hinge, the Fc fragment is assumed to retain the hinge and the disulfide linkages between the heavy chains, however, due to the high degree of interchain association between the heavy chain CH2-CH3 domains in the antibody, a dimeric structure is retained even in the absence of the disulfide (hinge) bonds. Thus, as used herein "Fc" refers to the dimeric structure formed by association of the heavy chain CH2-CH3 segments whether covalently linked or not. It will be understood that the non-covalently associated Fc may be distinguished from the disulfide linked Fc by its ability to undergo dissociation into CH2-CH3 monomers in the presence of a denaturant such as a detergent.

Human antibodies are immunoglobulins which basic structure is a dimer of two heterodimers, where the heterodimers are each comprised of a heavy and a light chain polypeptide.

The terms "proteolytic", "protease", "proteinase" and "proteolytic enzyme" are used interchangeably and mean an agent, e.g. enzyme, which is able to cleave a polypeptide chain producing two or more fragments, where the enzyme acts under normal temperature and under physiological conditions or physiologically compatible conditions. Physiological conditions include any temperature, buffer, cation, anion, substrate, catalyst, pH, cofactor, or the like which is naturally found in the body of a living mammal whether in health or disease. However, the protease may be derived from a non-mammalian source such as from a pathogen which may be of any type of life form. Proteases are hydrolases that act on peptide bonds.

By "scIgG" or "single cleaved IgG" is meant any immunoglobulin class G molecules having a heterodimeric structure comprising two heavy chains and two light chains, where one of the heavy chains has been subjected to proteolytic cleavage on a single heavy chain while the second heavy chain remains intact.

By "upstream" relative to an amino acid sequence written from the N-terminal to the C-terminal residue is meant the residues in the sequence towards the N-terminus from a given residue. Conversely, by "downstream" relative to an amino acid sequence is meant the residues in the sequence towards the C-terminus from a given residue.

Antibody Functions by Substructure

In general, immunoglobulins, antibodies are proteins which consist of regions of continuous polypeptide chains comprising approximately 100 amino acids, and each about 10-11 kDa, which show a characteristically folded globular domain and represent different elements of the structure. For immunogammaglobulins (IgGs), these domains are grouped together into segments; the Fab segment is comprised of a light chain variable joined to a light chain constant region in a single chain linked through a disulfide bond to the heavy chain first constant region (CH1) which is contiguous with the heavy chain variable region; Fc is comprised of two contiguous heavy chain constant regions (CH2 and CH3) linked through interchain disulfide bonds in the hinge region. Studies have shown that proteases, such as papain and pepsin, preferentially cleave antibodies at sites which are between the segments. Two identical Fab segments connected via the hinge region to one Fc segment, thus form a Y-shaped conformation of the 150 kDa structure (see FIG. 1). Fab segments generated using papain typically have a molecular weight of 46 kDa, nonreduced F(ab')$_2$ typically have a molecular weight of 90-100 kDa, and nonglycosylated, nonreduced Fc will have an apparent molecular weight of approximately 50-60 kDa. However, as each antibody species, and each subclass of antibody within a species, is slightly different, the exact nature and location of the cleavage and cleavage products are variant.

Antigen binds to antibodies via an antigen binding site in the variable domains of each pair of light and heavy chains (FIG. 1). Other molecules, known as effector molecules or cells, bind to other sites in the remainder of the molecule, i.e. other than the antigen binding sites, and this portion of antibody includes the more invariant immunoglobulin sequences, "the constant portion" of an antibody, such sites being located particularly in the Fc region constituted by the portions of the heavy chains extending beyond the ends of the light chains: the upper hinge, lower hinge, CH2 and CH3 domains.

Antibodies have several effector functions mediated by binding of effector molecules. For example, binding of the C1 component of complement to antibodies activates the complement system. Activation of complement is important in the opsonisation and lysis of cell pathogens (a process called complement-mediated cytotoxicity or CDC). The activation of complement stimulates the inflammatory response and may also be involved in autoimmune hypersensitivity. Further, antibodies bind to cells via the Fc region, with a Fc receptor site on the antibody Fc region binding to a Fc receptor (FcR) on a cell. There are a number of Fc receptors which are specific for different classes of antibody, including IgG (gamma receptors), IgE (eta receptors), IgA (alpha receptors) and IgM (mu receptors). Binding of antibody to Fc receptors on cell surfaces triggers a number of important and diverse biological responses including engulfment and destruction of antibody-coated particles, clearance of immune complexes, lysis of antibody-coated target cells by killer cells (called antibody-dependent cell-mediated cytotoxicity, complement-directed cytotoxicity, or ADCC), release of inflammatory mediators, placental transfer and endothelial cell reuptake (via neotal Fc receptor or FcRn) and control of immunoglobulin production.

The sequences around the hinge domain are conserved among IgG isotypes (SEQ ID NO: 1-4) and among mammalian species generally. The IgG1 (SEQ ID NO: 1) and IgG3 (SEQ ID NO: 1) isotype comprise a Leu-Leu pair that is a structural motif for binding to Fcγ receptor(s) and for Fc effector functions. Other residues downstream of the "hinge core" which typically comprises at least one cysteine separated by two non-cysteine residues, are also conserved.

Applicants have discovered that a cleavage product, scIgG, of human IgG1 is formed by human and bacterial proteases when proteolysis occurs on one of the two heavy chain polypeptides that comprise an IgG, while not disrupting the overall composition of the heterodimeric molecule. Secondly, applicants have determined through kinetic analysis of proteolytic attack on human heavy chain constant region-containing IgG molecules, that scIgG is likely the more abundant product of in vivo proteolysis found in the serum than are other fragments. The existence of scIgG as a proteolytic intermediate leading to F(ab')$_2$ during proteolysis of IgG has been noted previously for the MMP-3 enzyme (Gearing A J H et al, Immunol. Lett. 81: 41-48, 2002). Cleavage of IgG by a streptococcal protease, IdeS, was also noted to produce a product resembling intact IgG by size-exclusion chromatography (Vincents B et al, Biochemistry 43: 15540-15549, 2004). However, no functional characterizations of this intermediate were reported nor were methods for detecting the scIgG in biological samples provided.

Applicants have further demonstrated that, in vivo, scIgG, exhibits a serum half-life compatible with assessment of disease activity over a period of several days to months, thereby enabling the use of scIgG as a marker of latent or suppressed disease processes, or could be used to understand the recent natural history and response or recovery from a disease.

Briefly, applicants have discovered that the kinetics of proteolytic cleavage under physiological conditions lead to a larger proportion of proteolytically cleaved IgG being in the scIgG conformation than species which are products of multiple cleavage events, such as the F(ab')$_2$ (see FIG. 1). In the process of testing a large number of proteases, it was determined that the first cleavage of a heavy chain constant region in an intact IgG proceeds more rapidly than the second, a sequence that leads to a temporal accumulation of the singly cleaved species. This single cleaved version of the IgG molecule is indistinguishable from its intact parent in many ways (e.g. molecular size, antigen binding, ability to be recognized by protein A/G).

In accordance with the invention, applicants have generated reagents suitable for the detection of proteolytic cleavage products including F(ab')$_2$ and scIgG. The reagents of the invention generated using cleavage site analogue peptides of the invention, recognize human IgG1 cleavage products but do not recognize intact IgG.

Applicants have further demonstrated that antibodies recognizing IgG cleavage products retaining antigen binding specificity can restore effector functions such as CDC and ADCC to the cleaved IgG.

Proteolytic Enzymes and Disease Association

The applicants demonstrated that antibody cleavage products, including scIgGs, similar in size to those generated with in vitro enzyme panel, are detectable in inflammatory exudates such as synovial fluid from patients with rheumatoid arthritis. Further, scIgG can be detected in the serum of patients with a number of diseases in which localized proteolytic activity is a known characteristic of the pathology. The scIgG in these disease states is at higher concentrations than in healthy normal volunteers and is also higher than in the serum of patients with less severely inflammatory disease.

The detection of cleaved IgG including scIgG was accomplished by the generation of affinity-purified polyclonal antibodies (rabbit) that specifically bind to newly exposed epitopes in the cleaved heavy chain at or around the hinge disulfides, but do not react with the intact, non-cleaved IgG molecule. Confirmatory support for the detection of scIgG in serum is its prolonged circulating lifespan similar to intact IgG. The ability to detect scIgG in the bodily fluids, interstitial fluid, or blood of diseased individuals is a potentially novel biomarker strategy. It will be understood that other species of antibody besides rabbit (such as mouse, rat, and camel) may be used and monoclonal antibodies produced, for example, by cloning of an antibody gene coding for a specified antibody binding region sequence which polyclonal or monoclonal antibody retains the ability to bind human IgG1 cleavage products but that do not recognize intact IgG are encompassed as reagents of the invention. Other methods of producing antibodies, e.g. by selection from antibody domain libraries, are well known to those skilled in the art and may be used as a source of the antibodies of the invention.

Antibody Reagents

The antibodies of this invention can be prepared in several ways well known in the art using criteria and immunogens designed by applicants to raise or select antibodies useful in the practice of the invention.

In one aspect, the antibodies are conveniently obtained from hybridomas prepared by immunizing an animal with the observed cleavage fragments or cleavage site analogue peptides derived therefrom. Thus, the antibodies can be obtained by immunizing animals or screening antibody libraries with antibody cleavage fragments including F(ab')$_2$ and scIgG, or N-terminal truncations or structural analogs thereof. In one embodiment, the peptides used for generating the antibodies are selected from the 14-mer peptides fragments of IgG1 shown in SEQ ID NO: 5-11, where the C-terminal residue of the polypeptide or peptide represents the residue upstream (N-terminal side) of the cleavage site as shown in Table 1 of the residue cleavage pairs. Fragments comprising the hinge motif, e.g. -T-C-P-P-C- of IgG1 (residues 7-11 of SEQ ID NO: 1), will be multimeric due to disulfide bond formation, unless the cysteine residues (C) have been replaced with e.g. alanine (A) or serine (S) residues thereby creating a form of chemical homolog of the cleavage peptide.

In a specific embodiment, the antibody is generated using an 8-mer peptide (eight contiguous amino acids) corresponding to the sequence of amino acids on the amino terminal side of the MMP-3 cleavage site (TCPPCPAP, residues 7-14 of SEQ ID NO: 1), or extended peptides corresponding to the glutamyl endopeptidase site (TCPPCPAPE, residues 7-15 of SEQ ID NO: 1); or the IdeS site (TCPPCPAPELLG, residues 7-18 of SEQ ID NO: 1). When used as immunogens, the peptides can conveniently be covalently attached to keyhole limpet hemocyanin (KLH) via the N-terminus or through an added linker residue or peptide.

The antibodies can thus be obtained using any of the hybridoma techniques well known in the art, see, e.g., Ausubel, et al., ed., Current Protocols in Molecular Biology, John Wiley & Sons, Inc., NY, N.Y. (1987-2001); Sambrook, et al., Molecular Cloning: A Laboratory Manual, 2$^{nd}$ Edition, Cold Spring Harbor, N.Y. (1989); Harlow and Lane, antibodies, a Laboratory Manual, Cold Spring Harbor, N.Y. (1989); Colligan, et al., eds., Current Protocols in Immunology, John Wiley & Sons, Inc., NY (1994-2001); Colligan et al., Current Protocols in Protein Science, John Wiley & Sons, NY, N.Y., (1997-2001), each entirely incorporated herein by reference. An antibody of the invention can include or be derived from any mammal, such as but not limited to a human, a mouse, a rabbit, a rat, a rodent, a primate, or any combination thereof and includes isolated human, primate, rodent, mammalian, chimeric, humanized and/or CDR-grafted anti-integrin antibodies, immunoglobulins, cleavage products and other specified portions and variants thereof.

Phage-displayed antibody libraries may also be used to identify novel binding domains with the desired specificity to scIgG and other antibody fragments.

Figure 3:
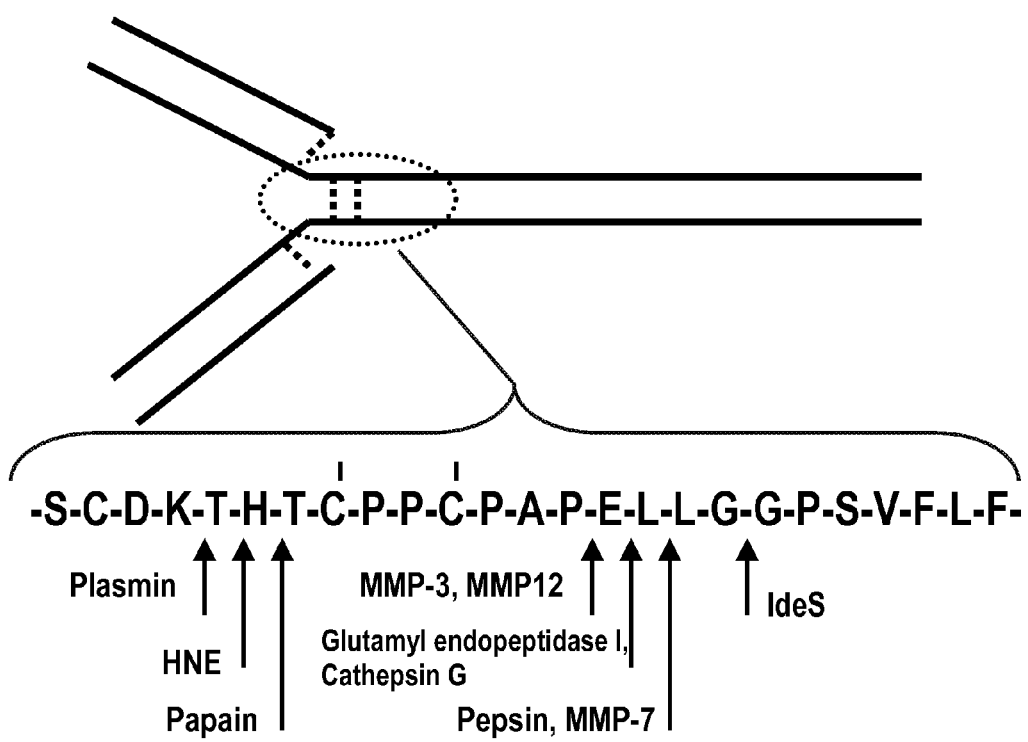
FIG. 3 shows the sequence of the human IgG1 heavy chain around the hinge region; the positions of major proteolytic cleavages are indicated by arrows.

In raising or selecting antibodies or other binders useful in the present invention, the specific reagents used for this purpose are a further aspect of the invention. The specific immunogens or test reagents developed for this purpose are characterized as comprising residues around the hinge core of the IgG1, including but not limited to the residues SCDKTH-TCPP CPAPELLGGP SVFLFP (SEQ ID NO: 1) as shown in FIG. 3. Hinge regions of other human isotype antibodies that produce antibody fragments upon contact with proteolytic enzymes may also serve as sources of peptides for the purposes of creating, selecting or testing antibodies or other binding molecules to enzymatic cleavage products. An analogous region of the human IgG4 heavy chain includes residues TCNVDHKPSN TKVDKRVESK YGPPCPSCPA PEFLG-GPSVF LF (SEQ ID NO: 2) and for IgG2 and IgG3 as shown in SEQ ID NOS: 3 and 4, respectively. In each case, the peptides consist of at least 5 contiguous amino acids selected from the human IgG hinge region sequences of SEQ ID NO: 1, 2, 3, or 4 that are on the amino terminal side of a protease cleavage site. In one aspect, the specific immunogen or peptide used for generating the antibodies comprise at least the hinge core of the IgG1, defined as the residues -C-P-P-C- or a analogue wherein the cysteine residues are replaced with serine residues. In a specific embodiment, the peptide is a 12-mer peptide analogue of the human IgG1 lower hinge and adjoining CH2 domain having the sequence TCPPCPA-PELLG (residues 7-18 of SEQ ID NO: 1).

A general method for creating peptide fragments useful in generating, selecting or testing antibodies or other binding molecules to proteolytic cleavage products is to a) identify the N-terminal residue of a pair of residues of an antibody heavy chain cleaved by a protease such as those exemplified by specific proteases in Example 1 and shown in Table 1, b) define from 5-14 or more upstream residues from that cleavage site where the N-terminal residue will become the C-terminus of the defined sequence and c) produce the peptide in sufficient amounts for the desired purpose(s). Optionally, any cysteine residues can be substituted with serine or alanine or other amino acid where no reactive side groups are present or reactive side group has been irreversible or reversible blocked. Peptides such as those described are those selected from SEQ ID NO: 5-11 or N-terminal truncations thereof. The peptides may be labeled, conjugated or cross-linked or used in admixture one with another or with adjuvants for the purposes of testing binding or as immunogens or panning targets for use e.g. in selecting binders from a phage display library.

The present invention further provides, in one aspect, isolated nucleic acid molecules comprising, complementary, or hybridizing to, a polynucleotide encoding the aforementioned specific peptides or antibodies thereto, comprising at least one specified sequence, domain, portion or variant thereof. The present invention encompasses isolated nucleic acids encoding at least one isolated monoclonal antibody having specificity for the scIgG as described herein and a nucleic acid vector comprising the isolated nucleic acid, and/or a prokaryotic or eukaryotic host cell comprising the isolated nucleic acid. The host cell can optionally be at least one selected from E. Coli, COS-1, COS-7, HEK293, BHK21, CHO, BSC-1, Hep G2, 653, SP2/0, 293, HeLa, myeloma, lymphoma, yeast, insect or plant cells, or any derivative, immortalized or transformed cell thereof. Also provided is a method for producing at least one antibody of the invention, comprising translating the antibody encoding nucleic acid under conditions in vitro, in vivo or in situ, such that the peptide or antibody is expressed in detectable or recoverable amounts.

Methods of Use

Diagnostics

The reagents of the invention are useful in detecting disease pathology when the disease process invokes, is a result of, causes, or is otherwise associated with proteolytic activity and proteolytic enzymes, proteases. Such diseases and processes include those precipitating or aggravating, produced by, or resulting from infection, stroke, vascular disease, myocardial infarction and several other acute and chronic inflammatory disorders. Applicants have demonstrated that one particularly useful biomarker of the proteolytic activity is scIgG, which is detected at increased levels in some of the aforementioned disorders. As scIgG is generated located at the site of the pathology or pathological process or infection, scIgG provides a unique and specific marker of such processes as a gauge of the involvement of specific tissues or cell types at the disease site.

In one embodiment of the method of the invention, a sample is obtained from a subject suspected of having, having had, or having been treated for a disease characterized by elevated levels of proteases. The sample is contacted with a binding agent, such as an antibody preparation, having specificity for IgG cleavage fragments known to result from contact between the disease stimulated protease and a population of serum IgG.

The method of the invention can be used to assess whether patients previously diagnosed with a disease or condition are at risk for advanced disease (e.g. cancer metastases, aggressive tumor growth, persistent infection, etc.).

In some cases, for example in the cancer patient, the detection of scIgG may be useful to indicate advanced disease progression involving metastatic spread which is known to involve elaboration of proteolytic enzymes, especially MMPs. In some aspects, neoplastic disease shares these mechanisms generally with inflammatory processes, tissue repair, and healing (Coussens, L. M. and Werb, Z. 2002. Nature 420 (19): 860-867). Other studies have shown that, for example, lipid lowering correlates both with a reduction in the risk for cardiac and vascular events, e.g. thrombosis, and with a reduction in MMPs such as MMP-2 and MMP-9 and that these enzymes are produced by atherosclerotic plaques (Deguchi, J, Maanori, A., Ching-Hsuan, T. et al. 2006 Circulation 114: 555-62). Thus, the methods of the invention are particularly applicable but not limited to patients with severe arthritic syndromes (RA, ankylosing spondylitis), certain cancers (especially inflammatory breast cancer), severe coronary arterial settings (myocardial infarction and congestive heart failure) and other diseases like asthma. The method of the invention may be used to distinguish those diseases and conditions in which the pathophysiology involves or induces protease capable of acting upon IgG from other pathologies not characterized by enhanced elevated levels of secreted proteases or wherein the proteases do not cleave IgG.

Thus, while the method of using the reagents described herein are specific for detection of the cleaved fragments, more specific analysis of the cleaved fragments could include an analysis of the binding specificity of the variable regions of the cleaved antibody. For example, a solid phase assay which combines antigen binding selectivity with fragmented antibody detection could be used to determine whether certain antigens and proteases are co-localized in a subject thereby providing information about the nature of the tissue, disease, or pathology at the site of proteolytic activity.

Drawing blood is the most frequently practiced form of tissue sampling from subjects, human or animal, healthy or ill. In so far as scIgG is found systemically, and is not restricted to the site of formation, that is, the site of the protease activity, it is a reporter marker for disease activity which may localized in specific compartments. One such compartment is the synovial fluid. Thus, blood or serum collection provides a convenient and feasible source for detection of early disease using the reagents and methods provided by the present invention. Alternatively, sampling of local settings like RA synovial fluid, lung exudates, biopsies, and the like could also be applied to patients at any stage including diagnosis or in patients with advanced disease. Cleaved antibody fragments may be detected in such tissue samples by direct staining (immunohistochemical methods) or in fractioned samples derived from the samples.

Tissue samples, including blood, should be treated so as to inhibit any residual active proteases. Chelation of metals (e.g. EDTA) effectively inhibits MMPs. Iodoacetamide blocks cysteine proteases (e.g. IdeS), serine proteases can be blocked with diisopropylfluorophosphate (DFP) and similar compounds. Active proteases are present in synovial fluid and the samples should be processed accordingly. Samples may also be maintained frozen until the time of assay. Once the samples have been appropriately processed, the scIgG specific reagents of the invention may be used in any antibody-based techniques such as ELISA, bead-based formats, RIAs, known to those skilled in the art or yet to be developed.

The anti-IgG proteolytic cleavage fragment reagents of the invention may be packaged in a kit for research or diagnostic use and for commercial sale along with other reagents such as buffers and standards such as intact human IgG and known quantities of cleaved IgG along with instructions for the measurement and, if desired, quantitation of IgG proteolytic cleavage fragments in tissue samples harvest from subjects.

Antibody Therapy

Antibodies of the invention immunospecific for a protease cleavage site or fragment thereof are capable of binding the remnants of enzymatically cleaved IgG which retain antigen binding domains, e.g. Fab, F(ab')$_2$, scIgG, and thus restore the Fc-related binding characteristics and attendant effector functions by providing intact functional Fc-region. Cleaved IgGs can function as antigens due to the existence of cryptic epitopes exposed after cleavage and thus can be used to generate antibodies that are specifically directed against cleavage points in both the upper and lower hinge region of IgG1 (but do not bind to intact IgG1). These antibodies are capable of restoring antibody-dependent cellular cytotoxicity (CDC) and antibody-dependent cellular cytotoxity (ADCC) effector functions to cleaved IgGs in vitro presumably by providing a surrogate Fc-region to the cleaved antibody.

Thus, the antibodies created by the methods taught herein or having the property of binding to proteolytically created antibody fragments in vivo may be useful as therapeutic molecules. The anti-IgG cleavage fragment antibodies of the present invention can be used to treat patients in which a disease characterized by disease induced proteolytic cleavage of IgG. In one aspect, the anti-IgG cleavage site fragment antibodies may be used to restore effector functions to antibody fragments which retain target specific binding capability.

The anti-IgG cleavage site antibody intended for therapeutic or prophylactic treatment of human disease or pathology may be prepared by the methods described herein above using the peptides of the invention as immunogens or selection reagents. Other binding domains specific for the cleaved IgG hinge region fragment may also be used to restore effector functions so long as the binding domain is associated with an Fc-domain capable of restoring the effector functions; which include CDC or ADCC, to an immunospecific IgG cleavage product. Of course, non-natural, modified or variant Fc sequences are also encompassed by the invention for the purposes of enhancing some FcR-driven interactions and attenuating others. Modified Fc regions are taught in, e.g. U.S. Pat. No. 6,737,056, U.S. Pat. No. 7,083,784, U.S. Pat. No. 7,317,091, U.S. Pat. No. 7,355,008, U.S. Pat. No. 7,364,731, U.S. Pat. No. 7,371,826, U.S. Pat. No. 7,632,497, U.S. Pat. No. 7,670,600, US20040002587A1, WO06105338A2, WO200905849, and WO2009086320.

Thus, provided within the scope of the invention are nucleic acid sequences, vectors, and host cells for the recombinant production of anti-IgG cleavage product antibodies or Fc-fusion proteins capable of binding a protease cleaved IgG and restoring effector functions.

Vaccination

Antibodies of the invention immunospecific for cleavage site specific fragments, capable of binding the remnants of enzymatically cleaved IgG which retain antigen binding domains, e.g. Fab, F(ab')$_2$, scIgG, and thus restoring the Fc-related binding characteristics and attendant effector functions of the antibody by providing a functional Fc-region, may be induced in a subject by immunization with a cleavage fragment peptide as disclosed herein. The anti-IgG cleavage product antibodies can be prepared by immunizing a host animal with a protease cleavage site specific peptide or proteolytically cleaved IgG fragments, and recovering the antibodies from the animals' serum. In such a method, the immunized animal is a source of the antibodies of the invention from which an antibody to be used as a reagent for a diagnostic test or, alternatively, to be used therapeutically, is prepared by methods described or known in the art. In a particular embodiment, a human subject is immunized with a protease cleavage site specific peptide or proteolytically cleaved IgG fragments and the anti-IgG cleavage product is generated in vivo. In one embodiment, the protease cleavage site specific peptide immunogen is selected from the group consisting of at least five (5) contiguous amino acids selected from the human IgG hinge region sequences of SEQ ID NO: 1, 2, 3, or 4 that are on the amino terminal side of a protease cleavage site such as the sequences of SEQ ID NOs. 5-11, N-terminal truncations and chemical homologs thereof.

The use of an cleavage site specific immunization or "vaccination strategy" will provide universal restoration of the inherent Fc-domain functions of IgGs independent of the origin of the protease (i.e. of bacterial origin or host origin in the case of proteolytically-enriched tumors) limited only to the specificity of the cleavage site specific antibody for the epitope formed by the residue specific cleavage within the IgG. An individual may be vaccinated with more than one cleavage site peptide or analogue peptide for a broader spectrum of antibody restorative capabilities, if so desired. Alternatively, a patient may be treated with a cleavage site specific antibody before, during or after being vaccinated to produce an cleavage site specific antibody response. In a particular embodiment, the individual is vaccinated with a disease specific cleavage site specific peptide or an analogue peptide before, concurrent with, or following the administration of a targeted antibody preparation designed to treat a given disease state where the targeted antibody activity involves effector function, and the antibody is subject to cleavage by one or more IgG cleaving proteases. In this manner, the effector function of the targeted antibody can be restored and the effect of the antibody treatment is enhanced or restored while the targeting function of the antibody has not been altered. In one embodiment, the disease being treated in a subject is characterized by elaboration of one or more IgG-cleaving proteases (see Table 1).

Methods of vaccination are well known in the art and, in particular, it is known that small antigens, or haptens, and linear peptides are more immunogenic when a plurality thereof are conjugated to a carrier molecule which may also be immunogenic such as keyhole limpet hemacyanin (KLH). Numerous conjugation methods are known in the art and are described, for example, by G. T. Hermanson in "Bioconjugate Techniques", Academic Press, 1996. Briefly, conjugations of a hapten to a carrier is generally effected by means of linkers or, more appropriately cross-linkers, which consist of linear molecules of various length bearing reactive functional groups at both ends. In homobifunctional linkers (i.e. glutaraldehyde) the two functional groups are identical: in heterobifunctional linkers, they are different. The detailed conjugation chemistries are well known. As the targeted IgG cleavage fragments retain the antigen specific binding domains associated with the N-terminus portions of the immunoglobulins (variable region, CH1 and, in some case, some of the core hinge) the antibody response should be directed to the portion of the analogue peptide representing a new C-terminus at the cleavage site. Therefore, it is desirable to conjugate the N-terminus of the analogue peptide and present a free C-terminal residue as the immunogen.

In a vaccination method, adjuvants (for example, aluminum-containing adjuvant (Alum), Incomplete Freund's Adjuvant (IFA), Complete Freund's Adjuvant (CFA)) can be used with the unconjugated or conjugated hinge region analogue peptides to direct the immune response to produce antibodies (humoral or Th2-driven) and direct the binding domains against the cleavage site specific fragments. CD40 agonists such as the natural ligand gp39 can be used to stimulate the immune response. A CD40 agonist that activates a CD40 receptor preferably on an antigen presenting cell, preferably a dendritic cell is one example.

Human Vaccines

Human vaccine preparations have been developed which are safe and effective. To enhance the immunogenicity of recombinant protein-based vaccines, adjuvants are required. The most widely used adjuvants are insoluble aluminium salts, generically called alum, such as boehmite and aluminium hydroxyphosphate. Alum adjuvants induce predominantly a Th2-type cytokine response (Lindblad, 2004; Raz & Spiegelberg, 1999; Valensi et al., 1994). Therefore, alternative adjuvants may be required for the successful development of a peptide vaccine.

Polymeric microparticle encapsulation of antigens have been evaluated as vaccine adjuvants (Eyles et al., 2003 J Drug Target 11, 509-514; Singh et al., 2004 Expert Opin Biol Ther 4, 483-491). Microparticles formed of poly(DL-lactide co-glycolide) (PLG) are well known in the art.

Various oil-in-water emulsions have also been developed as alternative adjuvants to alum. The most advanced of these is a squalene oil-in-water emulsion (MF59), which is a potent adjuvant with an acceptable safety profile. The influenza vaccine product called Fluad comprises MF59. Like alum, MF59 can promote antigen uptake by dendritic cells in vivo. Moreover, it has been shown that, after i.m. injection, MF59 is internalized by APCs that migrate to the lymph node. Besides promoting antigen delivery, MF59 might also act as a local pro-inflammatory adjuvant as it was observed to promote an influx of blood mononuclear cells after i.m. injection.

Other molecules that can be used in combination with alum, MF59, or microparticles include, but are not limited to; CpG to enhance Th1-type responses to vaccines, GM-CSF, and IL-2.

The prepared immunogen with or without admixed adjuvants or "vaccine" may be administered to the subject by any suitable route, such as but not limited to intradermally, subcutaneously, intranasally, and intramuscularly.

Various protocols may be used for vaccination. One protocol contemplated as one aspect of the invention is the prime-boost protocol wherein a first vaccine composition that comprises the desired immunogen, a prime vaccine composition, is administered in conjunction with a boost vaccine composition that comprises a corresponding immunogen that differs in form from the immunogen of the prime vaccine composition. The boost vaccine composition may be administered at the same time as the prime vaccine composition or it may be administered at some time following the initial administration of the prime vaccine composition. The prime and boost vaccine compositions may be administered via the same route or they may be administered via different routes. If the prime and boost vaccine compositions are administered at the same time they may be administered as part of the same formulation or as different formulations. Both the prime vaccine composition and the boost vaccine composition may be administered one or several times. Thus some doses of the prime vaccine may be administered after the administration of a dose of the boost vaccine. It is within the skill of one with ordinary skill in the art to optimize the vaccination protocol using these and other known or yet to be discovered variation of routes of vaccine administration and timing for vaccine administrations.

While having described the invention in general terms, the embodiments of the invention will be further disclosed in the following examples.

Example 1

Cleavage Analysis of Human IGG Heavy Chain

Proteolysis of human IgG heavy chain by matrix metalloproteases, cathepsins, human neutrophil elastase (HNE), and selected pathogen enzymes such as staphylococcal glutamyl endopeptidase (V8 protease), and immunoglobulin degrading enzyme of streptococcus (IdeS) was studied.

A purified monoclonal antibody comprising a human IgG heavy chain was contacted with the proteases described and sampling was conducted over various durations of contact. Fragmentation in the samples was evaluated using the Agilent microfluidics "lab-on-a-chip" technology for in vitro biosizing (Goetz H et al. Biochemical and Biophysical Methods 60; 281-293, 2004).

Antibody Substrates.

Monoclonal antibodies were either fully human, recombinant humanized murine antibodies or human/murine chimeric antibodies possessing human constant domains and hinge regions of the IgG1kappa class/subclass and species: Mab1 is a human IgG1 which binds a pathogen, Mab2 (anti-cytokine) is a human/murine chimeric IgG1 antibody possessing human constant regions and hinge domain, and Mab3 is a CDR-grafted humanized IgG1. All of the antibodies contain a kappa light chain.

Proteolytic Enzymes and Methods of Testing.

Human pro-MMP-2, MMP-7 and pro-MMP-9 were obtained from Chemicon International (Temecula, Calif.) and were activated by incubation with 1 mM p-aminophenylmercuric acetate (APMA; CalBiochem, San Diego, Calif.) for 16 hr at 37° C. prior to use (Marcy et al., 1991). Recombinant human active MMP-12 was obtained from R&D Systems. Recombinant MMP-1 was a generous gift from Dr. Hideaki Nagase. Human pro-MMP-3 was transiently expressed in HEK cells with a histidine tag in place of the hinge and hemopexin domains. The pro-MMP-3 variant was activated by incubation at 55° C. for 25 minutes as described (Koklitis et al., 1991). Cathepsins B, D, G, S and proteinase 3 were obtained from Athens Research & Technology (Athens, Ga.). The coagulation enzymes thrombin, F.Xa, F.IXa, F.XIIa and kallekrein, as well as plasmin and plasminogen, were purchased from Enzyme Research Laboratories (South Bend, Ind.). Tissue plasminogen activator (Activase) was a product of Genentech (South San Francisco, Calif.). Streptokinase and activated protein C were obtained from Sigma (St. Louis, Mo.). Staphylokinase was obtained from Affinity BioReagents (Golden, Colo.). *Staph. aureus* V8 glutamyl endopeptidase I was obtained from Pierce Biotechnology (Rockville, Ill.). Recombinant immunoglobulin degrading enzyme of *Streptococcus pyogenes* (IdeS) was provided by Dr. Lars Bjorck of the University of Lund (Lund, Sweden).

Proteinase digestions of purified IgGs were carried out at pH 7.5 in phosphate-buffered saline (PBS) or, for the metalloproteinases, in Tris-buffered saline buffer at 37° C. Calcium chloride was included in the metalloproteinase reactions at 1 mM for MMP-12 and 10 mM for MMP-3; otherwise no additives were used. Antibody concentrations were typically 1 or 2 mg/mL and reactions were initiated by addition of enzyme to a 1% (w/w) ratio to IgG. Aliquots (10-20 μL) were removed at indicated times and the reactions were stopped either by adjustment to 20 mM EDTA (metalloproteinase incubations) or to 1 mM iodoacetamide (cysteine proteinases) or by rapid freezing.

The major proteolytic cleavage positions in the IgG1 hinge were identified for enzyme-generated fragments by N-terminal sequencing of the purified Fc fragment (MMP-3 and MMP-12) and/or high resolution mass spectrometric analyses of the purified Fab (neutrophil elastase, plasmin) and F(ab')$_2$ (cathepsin G, glutamyl endopeptidase and IdeS) fragments. Fragmentation was evaluated using the Agilent microfluidics "lab-on-a-chip" technology.

Results. A list of proteinases that were examined and the results of the analysis of the primary products of proteolytic cleavage of human IgG1 is presented in Table 1. Several enzymes did not fragment IgG1 under the conditions used. Among the active proteinases, relative specific activities under the conditions described were: IdeS>MMP-12>MMP-3, glutamyl endopeptidase>neutrophil elastase>cathepsin G, plasmin>MMP-7.

Figure 2:
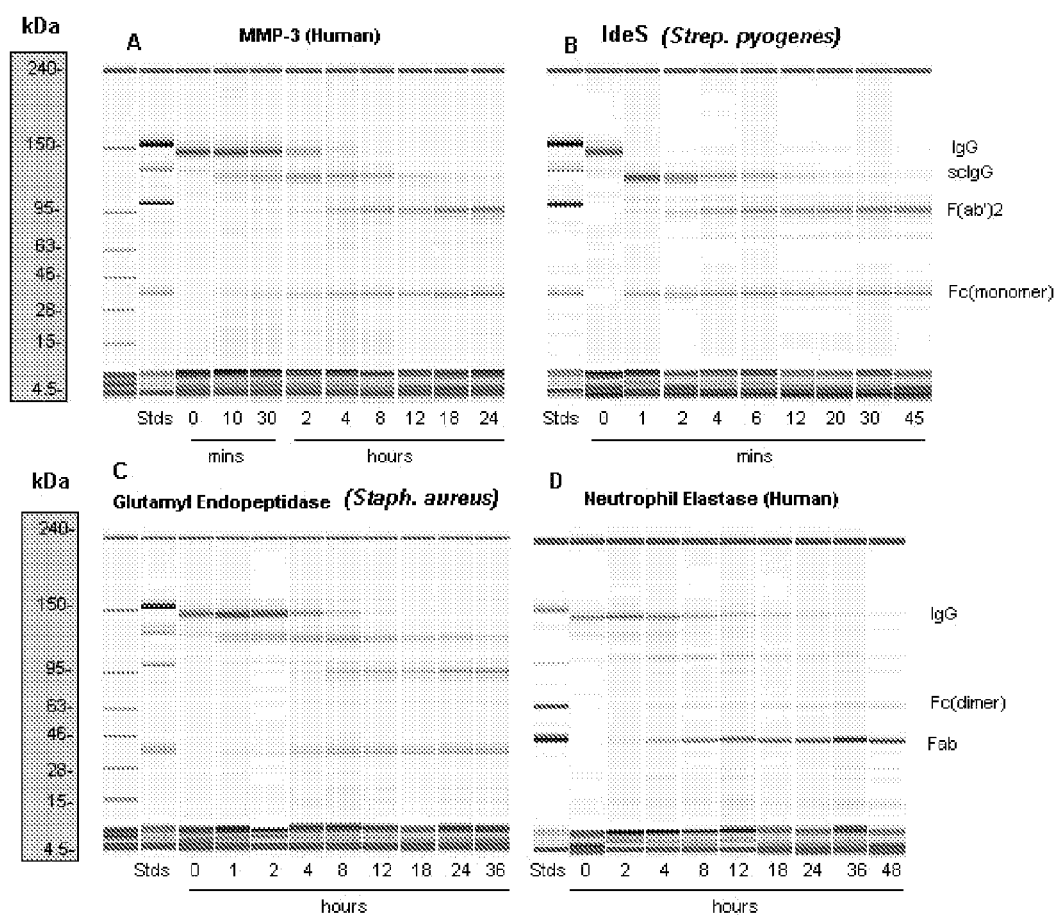
FIG. 2 shows four individual Agilent Biosizing microcapillary electrophoresis analyses as gel images at times during each of the proteinase digests of a human IgG1κ antibody, Mab1, by 1% w/w of human MMP-3 (A), streptococcal IdeS (B), staphylococcal glutamyl endopeptidase I (C) and human neutrophil elastase (D) at 37° C. Standards on each gel (lane 1) correspond to an intact human/murine chimeric IgG1 and known cleavage fragments.

FIG. 2 depicts biosizing analyses of IgG before and during proteolytic enzyme treatment. MMP-3, glutamyl endopeptidase I and IdeS were each observed to cleave IgG1 in a stepwise fashion (FIGS. 2A, 2B and 2C, respectively). In each case, an early intermediate of approximately 135,000 Da was generated which was subsequently converted to a species of approximately 100,000 Da. A fragment of approximately 35 kDa, presumably the Fc-derived monomer of the CH2-CH3 domains, was also formed during these reactions. The molecular weight (35 kDa) gauged by gel migration is larger than that predicted by the heavy chain fragment amino acid sequence which would be 211 to 215 residues (between residue 232 and 237 to the 447$^{th}$ residue at the C-terminus of the heavy chain) but consistent with the fragment containing the glycosylation site in the CH2 domain. The disappearance of intact IgG (160,000 Da) occurred over a period of several hours with MMP-3 and glutamyl endopeptidase I, and within a minute or less with IdeS under these conditions. All digestions were carried out under comparable conditions as described.

The 135 kDa intermediate was found to result from a single proteolytic cleavage in one of the heavy chains in the lower hinge domain. Under non-denaturing conditions, the intermediate is indistinguishable from intact IgG in certain physical properties, such as migration in size exclusion chromatography (data not shown). However in SDS gels, and the present micro capillary electrophoresis system, the cleavage fragment of the Fc region (CH2-CH3 domains of the heavy chain) separates from the rest of the structure to reveal the reduced size intermediate (135 kDa). The size of this species is consistent with a singly cleaved IgG as reported by Gearing (2002 supra). Extended incubation of IgG1 with any of the three enzymes resulted in conversion of the scIgG intermediate to the F(ab')$_2$ fragment and Fc.

Among the enzymes exhibiting the ability to cleave IgG1 of the different monoclonal IgG1-based substrates tested, was a consistent finding that the initial cleavage to the single-cleaved intermediate was relatively rapid, and extended times were required for the second cleavage to F(ab')$_2$ to occur. Also shown in FIG. 2D is a digest of Mab1 with human neutrophil elastase (HNE). HNE differed from the three enzymes above in that it cleaved IgG in the upper hinge to yield Fab fragment and a corresponding disulfide-linked Fc dimer.

The major proteolytic cleavage positions in the IgG1 hinge were identified for the purified Fc fragment (MMP-3 and MMP-12) and/or high resolution mass spectrometric analyses of the purified Fab (neutrophil elastase, plasmin) and F(ab')$_2$ (cathepsin G, glutamyl endopeptidase and IdeS) fragments. The amino acid sequence of the human IgG1 hinge region is presented in FIG. 3, with the identified positions of enzymatic cleavages indicated. Extended digestion with proteinases that cleaved in the upper hinge yielded two Fab fragments; enzymes that cleaved in the lower hinge (below the core hinge disulfide bonds) yielded F(ab')$_2$s.

The dominant sites of enzymatic cleavage was identified or confirmed for each enzyme including human MMP-3 and -12, human cathepsin G, human HNE, staphylococcal glutamyl endopeptidase I and streptococcal IdeS based on mass and an analysis of the mass of the F(ab')$_2$ fragment or the N-terminus of the Fc fragment, respectively (Table 1). Secondary cleavage sites were observed in some cases during extended incubations (e.g. cathepsin G and HNE), and it was uncertain if these are alternative cleavage sites for the indicated proteinase or the result of minor, protease contaminants in these enzyme preparations. The MMP-12 and HNE cleavage sites in IgG have not been previously reported. For other proteases, the identified major IgG cleavage positions agreed with previously reported results (Chuba, 1994; Diemel et al., 2005; Gearing et al., 2002; Vincents et al., 2004; Yamaguchi et al., 1995).

The cleavage positions differ slightly among the enzymes; with proteolysis occurring after proline-232, glutamic acid-233 and glycine-236 for MMP-3, V8 and IdeS, respectively. These minor differences in cleavage position are not large enough to impact the apparent molecular weight as detectable using the micro-capillary electrophoretic biosizing system (Agilent Technologies). Longer incubation times with MMP-3, V8 and IdeS allow the complete conversion to F(ab')$_2$ fragments. The digestion of IgG1 by HNE differs from the other proteases as it cleaves before the core hinge disulfides (cysteines 226 and 229) between threonine-223 and histidine-224 to yield a Fab product and disulfide linked Fc (see FIG. 2D).

The cleavage sites are based on EU numbering and relate to the residues shown in FIG. 3 and SEQ ID NO: 1 which encompasses from Ser$^{219}$ through Phe$^{243}$ of a human IgG1 class antibody. Several proteinases cleaved IgG1 below the hinge domain, and yielded F(ab')$_2$ fragments of slightly different lengths (spanning Ala$^{231}$ to Gly$^{237}$). Many of the IgG-degrading proteinases characterized in this study have been reported to be expressed, or to be abundant, at sites of inflammation (HNE, cathepsin G, MMP-12), in the tumor or wound-healing environment (MMP-2, MMP-3, MMP-7, MMP-9, plasmin), and at sites of infection (glutamyl endopeptidase, IdeS) (Dollery et al., 2003; Kilian et al., 1996; Rooijakkers et al., 2005; Schönbeck et al., 1999; Shapiro, 1999; Sukhova et al., 1998; van Kempen et al., 2006; Vincents et al., 2004)). For many cases, it is unlikely that the extracellular expression of specific proteinases is primarily directed toward host IgG; rather, their elaboration is associated with the physiology of disease (e.g. matrix metalloproteinases in the tumor environment). Nevertheless, these in vitro, purified enzyme/monoclonal antibody degradation studies indicated that human IgGs are not resistant to a number of proteinases with potential relevance to human disease.

For enzymes that converted IgG1 to F(ab')$_2$ (the majority), the cleavages were highly specific and self limiting (unlike pepsin digestion that reduces the Fc domain to small peptides). With the exception of IdeS, the rates of IgG1 cleavage with most of these extracellular proteinases were generally slower than that seen with pepsin under its optimal conditions (e.g. pH 4.0). Proteolytic fragmentation to F(ab')$_2$ proceeded via single-cleaved intermediates in a two-step process. The single-cleaved intermediate of IgG1 was previously proposed as a possible intermediate during digestion of IgGs with MMP-3 (Gearing et al., 2002) and with IdeS (Vincents et al., 2004). In the present studies, it was consistently observed that the first cleavage to the single-cleaved intermediate occurred relatively rapidly compared to the second, slower cleavage that yields F(ab')$_2$. The studies reported here focused on IgG1 because it is the predominant isotype of IgG in human circulation. A limited number of other human isotype experiments were carried out to determine relative susceptibilities to MMP-3 and IdeS. In these it was observed that IgG4 was comparable in susceptibility to IgG1, whereas IgG2 and IgG3 were more resistant under these conditions (data not shown). Comparable investigations of IgA, IgM, IgE, IgD degradation were not done.

Proteolytic cleavage information is summarized in Table 1, where "Coagulation proteinases" included F.XIIa, FIXa, F.Xa, thrombin and activated protein C; plasmin was plasminogen co-incubated with plasminogen activators; tPA, streptokinase and staphylokinase; "plasminogen activators alone" are without plasminogen; and the MMPs were recombinant proteinases obtained either as the active form or the proenzyme as detailed in the Materials; and "None" denotes no detectable cleavage in 24 hours. Except where indicated all enzymes where human. The residue designations are for the EU numbering system for the IgG1 antibody heavy chain where the 25 residues of SEQ ID NO: 1 corresponds to residues 219 through 243 of the complete mature heavy chain.

TABLE 1

| Enzyme | Source | Proteinase Type | Disease Association (Ref) | Cleaved Site | Major Product |
|---|---|---|---|---|---|
| Cathepsin G | Human Neutrophil granules | Serine endopeptidase | Emphysema, IPF, RA (2, 3) | $Glu^{233}$-$leu^{234}$ | $F(ab')_2$ + Fc |
| Cathepsin B | Human Neutrophil granules | Serine endopeptidase | | | None |
| Cathepsin D | Human Neutrophil granules | Serine endopeptidase | | | None |
| Neutrophil elastase (HNE, leukocyte elastase, PMN elastase) Pancreatic elastase | Human Neutrophil granules neutrophils | Serine endopeptidase | Amyloidosis, lung emphysema, cystic fibrosis, ARDS, RA, tumor invasion (2, 3) Pancreatititis (3) | $Thr^{223}$-$his^{224}$ | Fab + Fc |
| Proteinase 3 (myeloblastin) | Human Neutrophil granules | Serine endopeptidase | | | None |
| Tryptase | Human Neutrophil granules mast cells | Serine endopeptidase | Anaphylaxis, fibrosis (2) | | None |
| Chymase | Human Neutrophil granules mast cells | Serine endopeptidase | Inflammation, cardiovascular diseases (2, 3) | | None |
| Kallekrein | Human Neutrophil granules | Serine endopeptidase | | | None |
| Coagulation proteinases | Human Neutrophil granules | Serine endopeptidase | | | None |
| Plasmin (fibrinolysin) | Human Neutrophil granules | Serine endopeptidase | Cell migration (e.g. tumors)(2) Streptococcal infection (6) | $Lys^{223}$-$thr^{224}$ | Fab + Fc |
| Plasminogen activators alone | Human Neutrophil granules | Serine endopeptidase | | | None |
| Interstitial collagenase (MMP-1) | Human (fibroblasts, chondrocytes, | Metalloendo peptidase | RA, OA, IBD, IPF, aneurysms (1) | | None |
| Stromelysin (MMP-3) | Human (fibroblasts, chondrocytes, fibroblasts, chondrocytes, osteoclasts, macrophages | Metalloendo peptidase | RA, OA, atherosclerotic plaque, Crohn's disease, colitis, some tumors (1, 4) | $Pro^{232}$-$glu^{233}$ | $F(ab')_2$ + Fc |
| Matrilysin (MMP-7) | Human (fibroblasts, chondrocytes, glandular epithelial cells | Metalloendo peptidase | Invasive tumors (1, 4) | $Leu^{234}$-$leu^{235}$ | $F(ab')_2$ + Fc |
| Collagenase 2 (MMP-8) | Human (fibroblasts, chondrocytes, neutrophils | | Inflammation, RA, OA (1, 4) | | None |
| Macrophage metalloelastase (MMP-12) | Human (fibroblasts, chondrocytes, macrophages | Metalloendo peptidase | Inflammation, tissue destruction when over-expressed, aneurysms, atherosclerotic plaque (1) | $Pro^{232}$-$glu^{233}$ | $F(ab')_2$ + Fc |
| Cathepsin S | Human (fibroblasts, chondrocytes, | Cysteine endopeptidase | | | None |
| Glutamyl endopeptidase I (Glu V8 protease) | *Staph. aureus* | Serine endopeptidase | *Staph. Aureus* infection (2) | $Glu^{233}$-$leu^{234}$ | $F(ab')_2$ + Fc |

TABLE 1-continued

| Enzyme | Source | Proteinase Type | Disease Association (Ref) | Cleaved Site | Major Product |
|---|---|---|---|---|---|
| Immunoglobulin degrading Enzyme of *Streptococcus* (IdeS) | *Strep. Pyogenes* | Serine endopeptidase | *Strep. Pyogenes* infection (5) | $Gly^{236}$-$gly^{237}$ | $F(ab')_2$ + Fc |

Barrett A. J., Rawlings N. D. and Woessner J. F. (Eds.), Handbook of Proteolytic Enzymes Vol. 1, Elsevier, Amsterdam, 2004.

Barrett A. J., Rawlings N. D. and Woessner J. F. (Eds.), Handbook of Proteolytic Enzymes Vol. 2, Elsevier, Amsterdam, 2004.

Powers, J C. "Proteolytic Enzymes and Disease Treatment" 1982. In: Feeney and Whitaker (eds). Modification of Proteins: Food, Nutritional, and Pharmacological Aspects. Advances in Chemistry Series 198. ACS, Washington, D.C. 1982 pp 347-367.

Tchetverikov I., Ronday H. K., van El B., Kiers G. H., Verzijl N., TeKoppele J. M., Huizing a T. W. J., DeGroot J. and Hannemaaijer R., 2004. MMP Profile in paired serum and synovial fluid samples of patients with rheumatoid arthritis. Ann. Rheum. Dis. 63, 881-883.

Vincents B., von Pawel-Rammingen U., Björck L. and Abrahamson M., 2004. Enzymatic characterization of the streptococcal endopeptidase, IdeS, reveals that it is a cysteine protease with strict specificity for IgG cleavage due to exosite binding. Biochemistry 43, 15540-15549.

Sun H., Ringdahl U., Homeister J. W., Fay W. P., Engleberg N. C., Yang A. Y., Rozek L. S., Wang X., Sjobring U., Ginsburg D., 2004. Plasminogen is a critical host pathogenicity factor for group A streptococcal infection. Science. 305, 1283-1286.

Example 2

Cleavage of IGG in an Inflammatory Exudate

Inflammatory exudates and other such fluids are expected to possess proteolytic enzymes associated with the inflammation and wound healing. For this purpose, samples of wound fluid were obtained from Ethicon Inc.

First, an antibody substrate, which comprises human heavy chain constant domains was randomly biotinylated. Ten microL of the biotinylated substrate antibody was added to 190 microL of the wound fluid and incubated at 37° C. for 8-24 hours. At specified times, samples were removed. The starting IgG and samples from the various times were applied in separate wells to a 4-12% Bis-Tris gel and subjected to SDS PAGE. The separated bands were transferred to a nitrocellulose membrane and, following blocking with 0.1M Tris buffered saline containing 0.1% Tween 20 and 10% blocking grade milk ("Blotto"), the blot was developed using AVIDIN-D-horseradish peroxidase reagent followed by TMB (membrane) substrate.

Figure 4:
FIG. 4 is a western blot showing the time course of biotinylated murine/human IgG degradation by wound exudate.

As evidenced by the gel image shown in FIG. 4, there was a loss of intact IgG by 8 hr and the appearance of bands similar in size to the F(ab')2 and Fab standards. The results of this experiment indicate that proteolysis of IgG by enzymes in an inflammatory fluid occurs over a several hour period and yields fragments that correspond with fragments produced by in vitro proteolysis with purified enzymes.

Example 3

Preparation of Reagent

The determination of the presence of host (patient) antibody fragments produced by endogenous proteases requires a reagent which selectively binds to the cleaved IgG but not intact IgG. Both identification of the cleaved component and a quantitative difference between fragment content in samples from patients with disease as compared to the normal population should be able to be assessed using the reagent.

The detection of unknown, but likely small amounts of IgG fragments in solutions containing relatively high concentrations of intact IgG is difficult. Although scIgG has been noted as a possible IgG cleavage fragment (Gearing 2002 supra), quantitation in human samples has not been previously performed. For this purpose, reagents with the necessary specificity were generated in rabbits having with a high degree of specificity for cleaved but not intact IgG.

Three conjugated, and progressively longer single-chain peptide analogs of the human IgG1 hinge region were used for immunization (at Invitrogen Corporation). An 8-mer peptide corresponding to the sequence of amino acids on the amino terminal side of the MMP-3 cleavage site was covalently attached to keyhole limpet hemocyanin (KLH) via the N-terminus (TCPPCPAP, residues 7-14 of SEQ ID NO: 1). Extended peptides corresponding to the glutamyl endopeptidase site (TCPPCPAPE, residues 7-15 of SEQ ID NO: 1) and the IdeS site (TCPPCPAPELLG, residues 7-18 of SEQ ID NO: 1) were separately prepared as immunogens. New Zealand rabbits (two per immunogen) were immunized by subcutaneous injection of 0.2 mg conjugated peptide in complete Freund's adjuvant and re-boosted three additional times with 0.1 mg antigen in incomplete Freund's adjuvant on days 14, 42 and 56. Serum was collected at 4, 8 and 10 weeks and pooled per immunogen for antibody purification. The immune titers were monitored by an ELISA based on solid phase antigen peptide.

Affinity purification of antibodies employed the respective peptide antigens immobilized on an activated support. The antiserum from the two rabbits immunized with the same antigen was pooled and passed through the antigen column after which the column was extensively washed. Specific antibodies were eluted as low affinity and high affinity pools using 3M KSCN and 0.1M glycine, pH 2.5, respectively. The two pools yielded indistinguishable binding characteristics and were used interchangeably and/or pooled. The three separately eluted pools of bound antibodies were next subjected to a second affinity adsorption step, this time on a column containing an intact antibody comprising human IgG1 heavy chain constant regions (Mab3). The intent of the second affinity chromatography step was to remove undesirable antibodies that might recognize intact IgG. However, little or no rabbit antibody was adsorbed to the IgG column suggesting that the population of antibodies was reactive only with the "cleaved" sequence with its exposed carboxy terminus.

Figure 5:
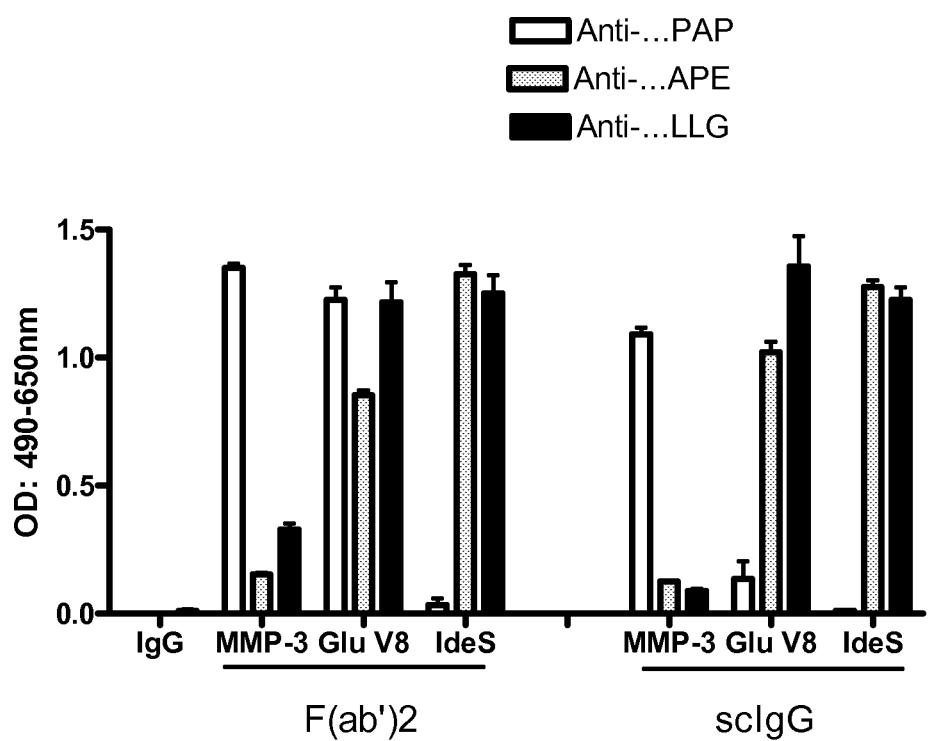
FIG. 5 a graph showing the relative specificity of the antisera generated in rabbits immunized with fragments of human IgG enzymatically generated from three different proteases: MMP-3, V8, and IdeS. Rabbits were immunized with conjugated peptides having the sequences TCPPCPAP, residues 7-14 of SEQ ID NO: 1 corresponding to the MMP-3 cleavage site; TCPPCPAPE, residues 7-15 of SEQ ID NO: 1 corresponding to the glutamyl endopeptidase site; and TCPCPAPELLG, residues 7-18 of SEQ ID NO: 1 corresponding to the IdeS site. ELISA reactivity of three individual rabbit polyclonal anti-cleavage site specific peptide antibody preparations were tested for their ability to bind with F(ab')$_2$ fragments of Mab3 IgG1κ, as well as ScIgG and intact IgG. The F(ab')$_2$ fragments were generated with human recombinant MMP-3, staphylococcal glutamyl endopeptidase I and recombinant IdeS from Strep. pyogenes. The antibody preparation showed binding to scIgG and F(ab$^1$)$_2$ but not to intact IgG. Bars correspond to the mean±standard deviation of three replicate wells.
Figure 6:
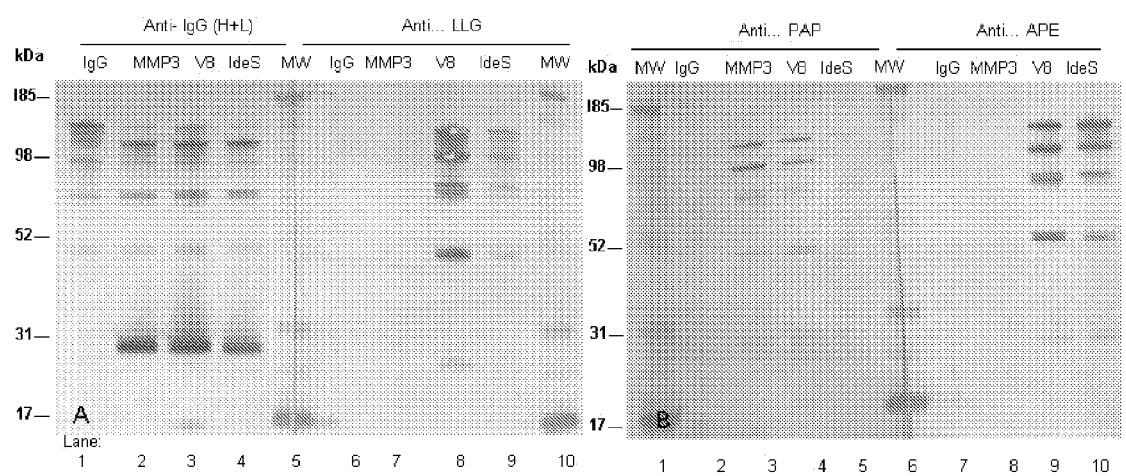
FIG. 6 is a Western blot showing the reactivity of rabbit polyclonal antibody preparations with antibody digests: Mab3 human IgG1 intact or that had been partially digested with MMP-3, glutamyl endopeptidase (V8) or IdeS was separated by SDS-PAGE followed by immunoblotting, where (A) was blotted with anti-human IgG (H+L) [lanes 1-4] or anti . . . LLG rabbit polyclonal [lanes 6-10]. (B) was blotted with anti . . . PAP [lanes 2-5] or anti . . . APE [lanes 7-10]. The blots were cut prior to incubation with antibodies through lane 5 in panel A and lane 6 in panel B to allow for detection with the individual antisera.

The individual affinity-purified rabbit anti-peptide antibodies were tested for their ability to bind to enzymatically-generated fragments of human IgG as well as intact IgG by ELISA (FIG. 5). The purified antibodies from the rabbits immunized with KLH conjugated to residues 7-14 of SEQ ID NO: 1 (the MMP-3 site analogue ending in PAP) did not bind intact IgG and were highly specific for scIgG and F(ab')$_2$ produced by digestion of IgG with MMP-3. This antibody preparation showed minimal reactivity to scIgG and F(ab')$_2$ produced with V8 protease or IdeS. In contrast, the antibodies obtained from rabbits immunized with the V8-cleavage site specific peptide analogue (residues 7-15 of SEQ ID NO: 1 ending in APE) and the IdeS-cleavage site specific peptide analogue (residues 7-18 of SEQ ID NO: 1 ending in LLG) showed a cross-reactive binding profile for scIgGs and F(ab')$_2$ produced by either of these two enzymes. However, these preparations showed minimal reactivity for the MMP-3 digested products. None of the antibody preparations bound to intact IgG and none of the antibody preparations was comparably reactive with fragments, including F(ab')$_2$ and scIgG, produced by three different enzymes as shown in FIG. 6.

The intended use of the cleavage site specific reagent is the detection of scIgGs and F(ab')$_2$ (and other potential fragments) that are produced in complex in vivo settings by enzymes present in disease specific tissues or produced by disease specific cell types or cell populations, e.g. infiltrating macrophages or neutrophils. For optimal coverage of potential IgG fragments, it was considered preferable to have as broad a profile of cleavage site recognition as possible. For this reason, a mixture of each of the three rabbit antibody pools was prepared at 0.33 mg/mL of each component (total=1 mg/mL) for use in subsequent Western blotting and serum-based ELISA tests. This pooled reagent is referred to as RAH-1.

Example 4

Single Chain Cleaved Immuoglobulin Assay

The novel assay employed for detecting scIgG in serum using, as a capture reagent, the RAH-1 capable of binding cleaved human IgG but not intact human IgG is described in detail as follows.

Using a Chemiluminescence ELISA, regions of a Nunc Chemiluminescence 96-well plates were coated with RAH-1 at 10 mg/ml in PBS. The rest of the plate was left un-coated (1×PBS alone). The plates were incubated at 4° C. over night. Plates were washed and 200 microlmicroL/well of Chemicon International's ChemiBLOCKER (C#2160) was added to the plates and incubated at 37° C. for 30 minutes. The blocking buffer was aspirated from the wells and the standards and samples were added to the plate. The standard Mab3, scIgG digested with V8, was added in duplicate starting at 50 mg/ml in PBS containing 1% Casein and 3% BSA using serial four-fold dilutions. The disease serum samples were added at a 1:50 dilution in the same buffer. Plates were washed and a 1:6000 dilution of Jackson Immuno Research's HRP conjugated AffiniPure F(ab')$_2$ Fragment Donkey anti-human IgG (H+L) which has minimal cross reactivity to various animals including rabbit was added to all wells. This was added in a dilution of PBS with 1% Casein and 3% BSA and incubated at 37° C. for 1 hour. The plates were washed thoroughly and 100 ml/well of HRP substrate (Roche's BM Chemiluminescence POD, 582 950) was added seconds before plate was read on the luminescent reader.

The average luminescence from the 0 ng/ml scIgG wells on the standard curve was subtracted from all wells that were exposed to the RAH-1 coat. This subtraction controls for any non-specific reactivity of the secondary with the RAH-1. Then, the value for each donor on non-RAH coated wells was subtracted from the previously-adjusted value of the RAH coated wells. This accounts for any non-specific reactivity in the serum to the plate.

Example 5

Use of Reagent to Detect Disease Associated Proteolytic Activity

The RAH-1 reagent was tested for its ability to detect IgG fragments in another inflammatory fluid, the synovial fluid of a patient with rheumatoid arthritis (RA).

Figure 7:
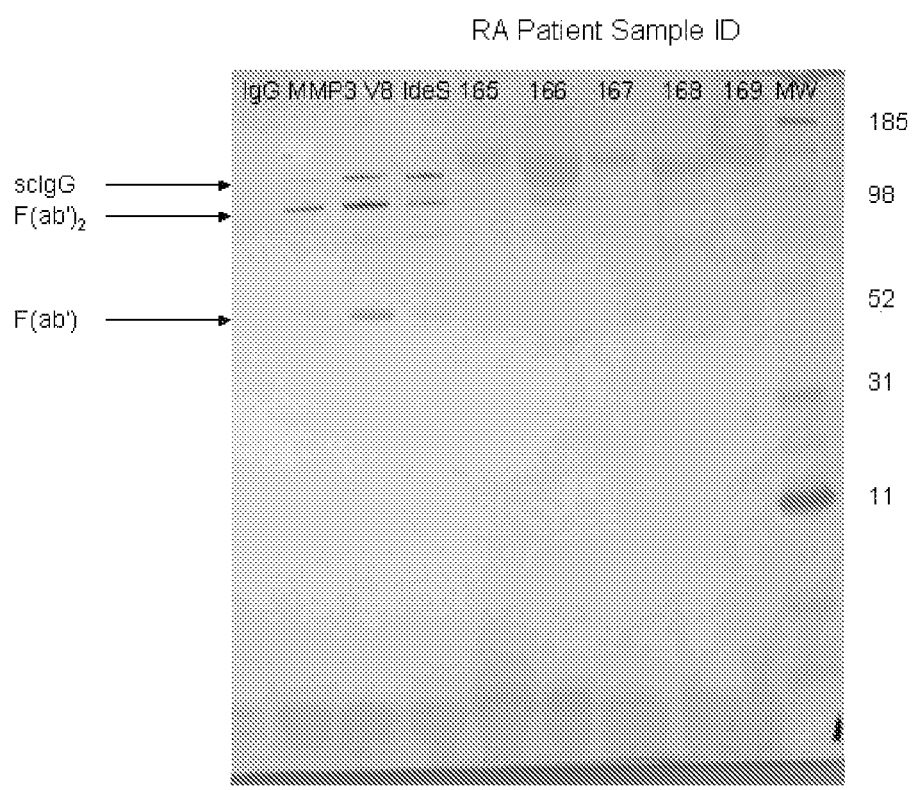
FIG. 7 is a western blot developed using the RAH-1 reagent on samples from an analysis of IgG degradation in the synovial fluid from 5 RA patients and compared to samples from in vitro proteolytic digests of a monoclonal IgG1 with MMP-3, glutamyl endopeptidase (V8) and IdeS.

A collection of synovial fluid samples from RA patients were purchased commercially from Bioreclamation. Samples were diluted 1:5 in LDS sample buffer and 10 microL of each sample loaded onto a 4-12% Bis-Tris gel. As a control for the reactivity of RAH-1, intact IgG (Mab3), or protease digested IgG (partial digests of Mab3 with MMP-3, glutamyl endopeptidase and IdeS) was loaded onto the gel as well. Following SDS-PAGE, the gel was transferred to nitrocellulose membrane and blocked with Blotto. The membrane was then incubated with a 1:2,500 dilution of the RAH-1 in blotto, washed with 0.1M tris buffered saline, pH 7.5 containing 0.1% Tween 20 and incubated with a 1:5,000 dilution of goat anti-rabbit IgG (H&L) horseradish peroxidase conjugate. The blot was then developed using TMB membrane. As shown in FIG. 7, the RAH-1 preparation did not react with the intact IgG, but detected scIgG, F(ab')$_2$ possibly Fab' from all 3 protease digests. For all five synovial fluid samples from RA patients, a band was detected at the approximate size of scIgG, F(ab')$_2$ and Fab', suggesting that these proteolytic fragments were present within the synovial fluid from individuals with RA.

Example 6

Use of Reagent to Monitor Disease

Blood plasma or serum is a more convenient for biomarker testing than biological fluids or tissue extracts, such as synovial fluid. However, the advantage of synovial fluid is that it is a self-contained and local environment in which the proteases are active and in which the IgG fragments might be expected to accumulate as described in Example 2. Nevertheless, the ease and prevalence of serum for testing makes it a considerably more likely sample tissue for biomarkers, including IgG breakdown products.

Before initiating testing for IgG fragments in different types and sources of serum, it was desirable to establish which if any of the proteolyzed IgG fragments would circulate for a sufficient period to allow its accumulation and quantification. To answer this question, a comparative pharmacokinetic study was designed. The following PK experiment in mice was modeled on several similar previously reported studies in which human IgGs generally exhibit terminal half-lives of 10-20 days.

Fractionated proteolysis products, Mab2 IgG1, and the scIgG and F(ab')$_2$ generated with MMP-3, were prepared as follows. A 20 milligram quantity of Mab2 IgG was digested with heat-activated MMP-3 as described in Example 1. The digestion was initiated by addition of enzyme to a 4 mg/mL solution of Mab2 in tris-buffered saline containing 10 mM $CaCl_2$, pH 7.5 at 37° C. The reaction was terminated by the addition of EDTA to a final concentration of 20 mM at 48 hours. There was no residual intact IgG and the percent of scIgG, F(ab)$_2$ and Fc was 24%, 41% and 36%, respectively, based on Agilent bio-sizing analysis (8862-67). The terminated digest was subjected to a two-step purification to remove the Fc fragment and to separate purified scIgG and F(ab)$_2$. In the first step, the digest was subjected to chromatography using protein A-Sepharose. The unbound material from the column contained the F(ab')$_2$ fragment and no detectable intact IgG or scIgG. Treatment of the column with 0.1M sodium citrate, pH 3.5, resulted in the elution of a mixture of Fc-containing components, the Fc fragment and scIgG. The fractions were immediately neutralized to pH 7 by the addition of $\frac{1}{10}^{th}$ volume of 2M Tris, pH 7.0. The neutralized material was concentrated to approximately 1 mL and dialyzed into phosphate-buffered saline, pH 7.5. The Fc fragment was separated from scIgG by size exclusion chromatography on Superdex 200 (column volume=100 mL). Two peaks eluted from the column, which were subsequently identified using the Agilent biosizing technique previously described as a 135 kDa conforming to the gel band position of scIgG and a lower molecular weight peak identified as the Fc monomer fragment of approximately 35 kDa. The purified scIgG and F(ab')$_2$ components were contacted with ActicleanEtox (0.5 mL of gel per 5 mL of each protein solution) to reduce endotoxin to AALAC specifications for allowable intravenous injection in mice (<40 EU/kg).

For the pharmacokinetic study, the equivalent milligram amount (1.9 mg/kg) of intact mouse-human chimeric monoclonal antibody, Mab2 IgG1, and the scIgG and F(ab')2 generated with MMP-3 was tested as described below.

A group of twenty-one female Balb/c mice (Ace Animals) were used for the pK study. Terminal bleeds were taken via cardiac puncture from three randomly selected mice prior to the experiment to serve as baseline controls. The remaining eighteen female Balb/c mice were weighed and placed into six equal groups. Two groups were injected with intact Mab2 IgG1, two groups with Mab2 scIgG1 produced with MMP-3 and two groups with Mab2 F(ab')'$_2$ produced with MMP-3. All injections were i.p. at a constant dose volume of 10 ml/kg based on individual animal weight at 0.19 mg/ml. Therefore, each animal received a 1.9 mg/kg dose at day zero. Approximately 80 microl of blood was collected at 1 h, 24 h, 7 d, 21 d, 35 d from the first of the two groups and at 5 h, 48 h, 14 d and 28 d from the second group The serum samples were stored at 20° C. until tested.

Figure 8:
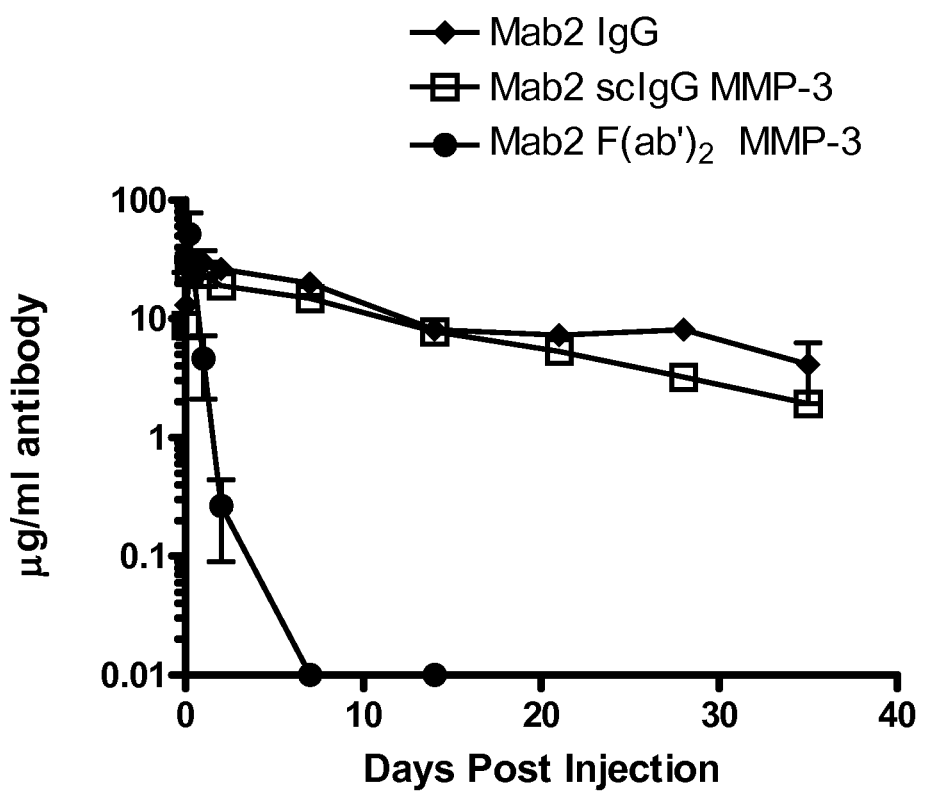
FIG. 8 shows the serum concentration over time of various proteolytic cleavage fragments, intact IgG, scIgG and F(ab')$_2$; after injection of the specified purified fragments into mice, measured using the goat anti-human IgG (H+L).

The IgG and IgG fragment concentrations of the collected serum was quantified via enzyme-linked immunosorbent assay (ELISA). A 0.5 microg/ml dilution in PBS of Jackson Immuno-research: Goat Anti-Human IgG, F(ab')$_2$ fragment specific (with minimal cross-reactivity to bovine, horse and mouse serum proteins) was used to coat Costar 3369 plates. Plates were blocked with PBS/casein/BSA. Following blocking, standards and samples were added in a PBS/1% casein/ 3% BSA. Standards included serial dilutions of the following: a murine/human IgG1, murine/human scIgG1 MMP-3 or murine/human F(ab')2 MMP-3 starting at 1000 ng/ml Each time point sample was serially diluted from 1:10 to 1:163,840 in PBS/1% casein/3% BSA. Human IgGs bound to the plates coated with anti-human capture antibody were detected with 50 ul/well Jackson Immuno-research: Goat Anti-Human IgG (H+L) (with minimal cross-reactivity to bovine, horse and mouse serum proteins; 109-035-083) and incubated for one hour at RT. The plates were thoroughly washed and exposed to 50 microl O-phenylenediamine (OPD) substrate for approximately 10 mins and stopped with 50 ul/well 3M HCL and read at 490-650 nm. The results are shown in FIG. 8.

The results of the mouse PK experiment indicate that the scIgG possesses an extended circulating lifetime, but that the F(ab')$_2$ does not. The very rapid clearance of F(ab')$_2$ in the mice is consistent with the rapid disappearance of this fragment in humans (Roskos L K et al. Drug Dev. Res. 61: 108-120, 2004). These results point to scIgG as the most abundant, long-lived, and useful proteolytic component of IgG for biomarker purposes.

Example 7

Proteolytic Enzymes in Disease

In order for the scIgG to be a useful disease biomarker, it must exhibit differential quantity in samples obtained from patients in defined disease categories as compared to healthy people.

A commercial source of serum from diseased individuals was identified as Genomics Collaborative (now SeraCare Life Sciences Inc.). Small volumes (300 microL) of serum from 10 different individuals within each of 8 diseases were purchased. The disease categories were rheumatoid arthritis, osteoarthritis, asthma, type-1 diabetes, breast cancer, lung cancer, myocardial infarction, and congestive heart failure. In addition, serum from 28 age-matched and gender-matched normal healthy volunteers were obtained from this vendor as controls.

Figure 9:
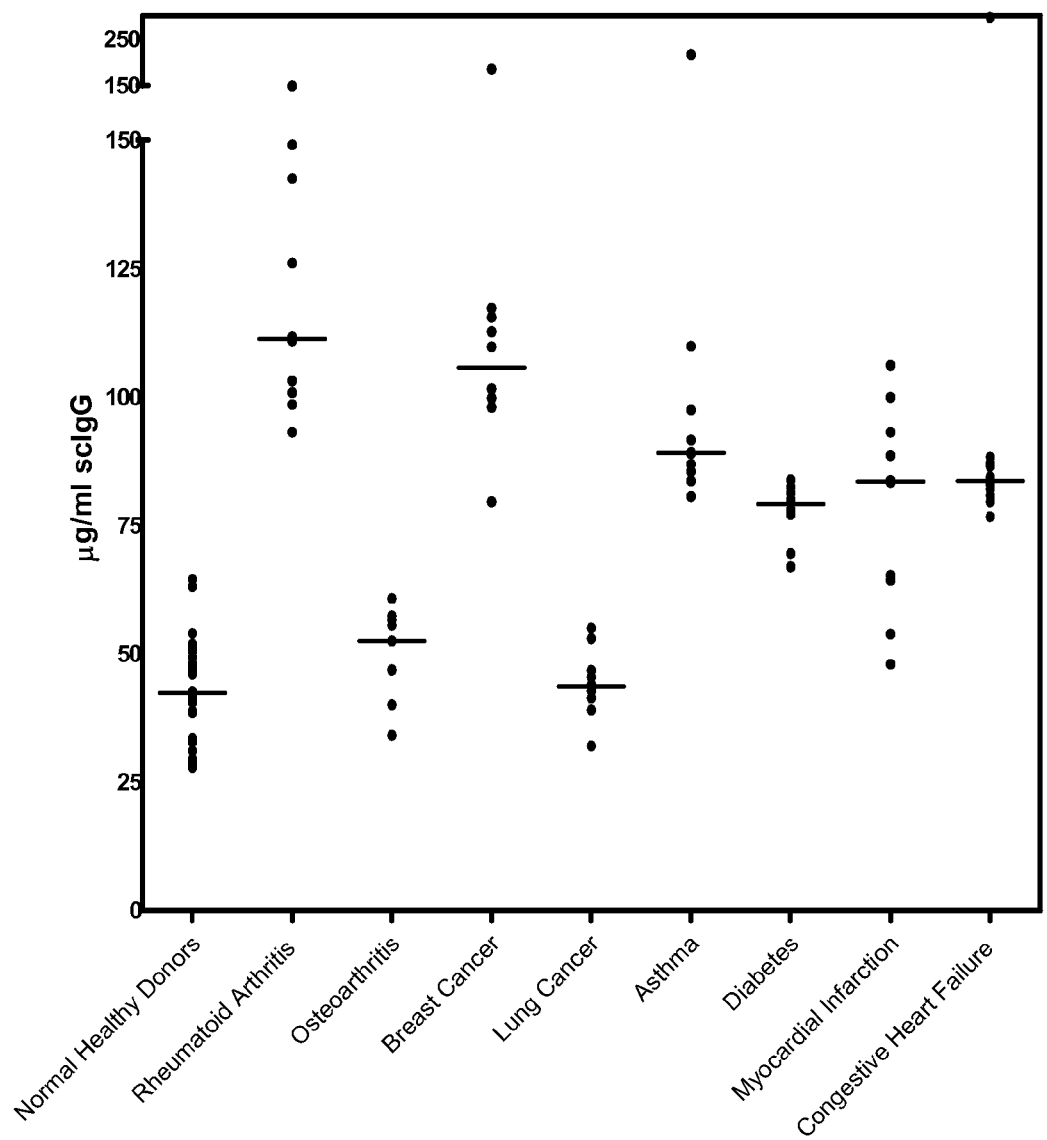
FIG. 9 is a dot plot of the individual values of scIgG detected by the reagent RAH-1 in human serum samples from patients diagnosed with the diseases as indicated as compared to that in a group of normal human serum samples where the lines indicated mean values in each group.

Using the assay as described in Example 4, the samples were analyzed and the results shown in FIG. 9. The assay, based on the selectivity of the RAH-1 reagent, demonstrated that IgG cleavage products comparable to those generated by known specific proteases are clearly detectable and above levels maintained in healthy or normal donors for an inflammatory autoimmune disease, rheumatoid arthritis. In contrast, patients with osteoarthritis showed levels which were similar and in the range of those for the normal individual's samples.

Example 8

Modified Single Chain Cleaved IGG Assay

A solid phase assay, ELISA, using reagent RAH-1 for detection of scIgG in serum was described in Example 4. In order to optimize the detection range for scIgG concentrations serum samples specific changes were made.

The plates used were Immulon 4 HBX plates (VWR) coated with rabbit polyclonal antibodies (RAH-1) at a concentration of 5 µg/mL in PBS pH 7.2 (100 µL per well) by sealing and incubating the plate for 1 hour at room temperature. Thereafter, the plate is washed 3× with PBS, 0.05% Tween (Sigma) on automatic plate washer. All samples and standards are diluted with PBS containing 1% BSA, 0.05% Tween. Anti-IgG Fc-Biotin (USBiologicalsUS Biologicals, Swampscott, Mass.) is the means of detection of scIgG standards or scIgG unknowns in serum dilutions.

The plate is blocked using 200 µL of SuperBlock (Pierce) for 15 minutes at room temperature (RT) with shaking and then washed plate 3× with PBS, 0.05% Tween on an automatic plate washer.

The standard material; Mab1 protease digestion product, is added to duplicate wells starting at 600 ng/mL (100 µL per well, 3 fold dilutions). Serum samples are diluted 1:100, 1:200, 1:400, etc. as appropriate). Samples are added in duplicate at the same time and incubated for one hour at RT on a shaker followed by 3× washing with PBS, 0.05% Tween on an automatic plate washer.

The IgG Fc Biotin dilution of 1:20,000 (dilute appropriately in assay buffer), is added to all wells at 100 µL per well and incubated for one hour at RT on a shaker followed by 3× washing with PBS, 0.05% Tween on an automatic plate washer.

SA-HRP (Streptavidin conjugated to horseradish peroxidase, Sigma, used at a 1:30,000 dilution in PBS, 0.05% Tween, 1% BSA) is added to all wells (100 µL per well and incubated for one hour at RT on a shaker followed by 3× washing with PBS, 0.05% Tween on an automatic plate washer.

Finally, 100 µL of TMB (3,3',5,5'-Tetramethylbenzidine a peroxidase substrate) as provided by the manufacturer (Sigma) is added to each well and allowed to incubate for about 10 minutes for color development. The reaction is stopped with 75 µL of 1 N $H_2SO_4$ and read plate at 450 nm.

Using the above ELISA format, the assay demonstrated greatly improved linearity and spike recoveries of scIgG in normal, healthy serum. The dilution linearity of the assay was determined in two serum pools, diluted 1:100 then spiked with Mab1 at concentrations of 150 ng/mL and 300 ng/mL, and further diluted to concentrations of 0, 25, 75, and 100% serum. Each sample dilution was assayed in triplicate and mean analyte recoveries were calculated. Linearity was assessed by calculation of an $R^2$ correlation coefficient from a plot of the observed (y-axis) versus expected (x-axis) analyte recovery results for each sample pool. The $R^2$ values were: Sample 1 Low 0.9983; Sample 1 High 0.9913; Sample 2 Low 0.9852; Sample 2 High 0.973; and dilution linearity was 100% for all dilutions.

Example 9

Detection of Single Cleaved IGG in Serum

Serum from RA patients was used exclusively in order to further study the results in Example 4 where some serum samples from this group of patients had notably higher scIgG compared to controls.

Figure 10:
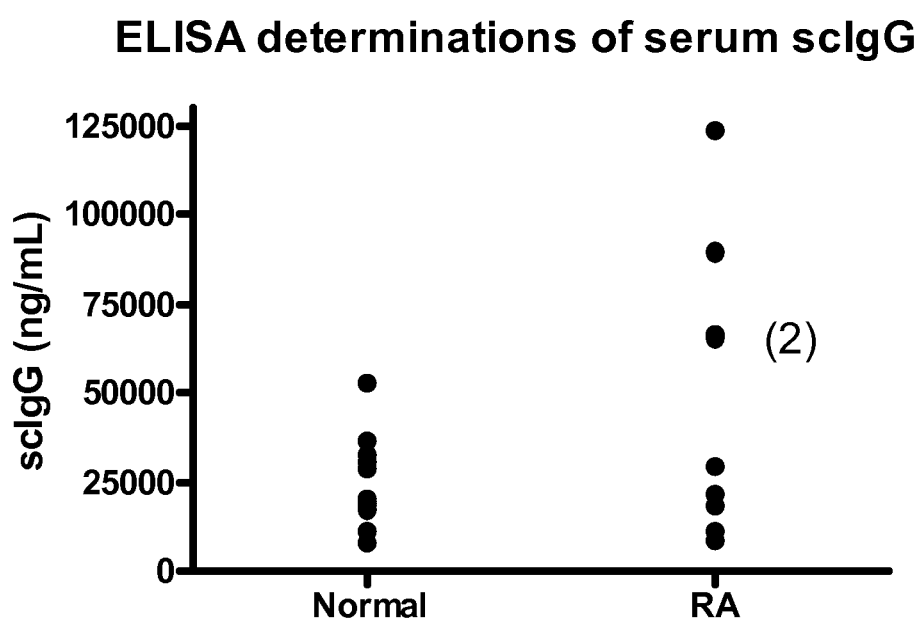
FIG. 10 shows the concentration of scIgG in diluted serum of 10 individuals with rheumatoid arthritis (RA) and an equal number of healthy, normal controls detected with reagent RAH-1 using an improved version of the ELISA; "(2)" in the RA group signifies that the same value was obtained in two separate individuals.

Serum samples from 10 subjects with rheumatoid arthritis (RA) and from 10 age- and gender-matched healthy individuals were obtained from Genomics Collaborative. Using the modified assay described in Example 8, the samples were analyzed and the results shown in FIG. 10. The results indicated that 4 of the 10 subjects with RA demonstrated serum scIgG concentrations >60 µg/mL. In the healthy control group, scIgG concentrations ranged from <8.2 µg/mL to 52.7 µg/mL. The samples for this comparison were not rigorously selected for stage of disease, treatment regimens, etc. Thus, it can be anticipated that further discrimination of healthy and disease-related serum scIgG might occur in longitudinal analyses of patients from well-controlled and prospectively designed clinical trials. However, the present assays on these commercial samples suggest that elevated scIgG concentrations can be detected in patients with disease.

Example 10

Preparation of Cleavage Site Specific IGG Monoclonal Antibody

It would be desirable to produce a defined molecule, such as a monoclonal antibody, for manufacture and potential use in human patients which binds cleaved IgG and not intact IgG. The following procedure represents a method for generation of such a molecule.

A 12-mer peptide analogue of the human $IgG_1$ lower hinge region and adjoining CH2 domain was the immunogen: TCP-PCPAPELLG (residues 7-18 of SEQ ID NO: 1) which is a peptide analogue of the IdeS cleavage site of human IgG1. The naturally occurring cysteines were replaced by alanines to give the variant TAPPAPAPELLG (SEQ ID NO: 12). An N-terminal cysteine was added to allow for conjugation to keyhole limpet hemocyanin (KLH) by standard chemical methods for reaction to free sulhydryls.

New Zealand white rabbits (3) were immunized with 0.5 mg KLH peptide in complete Freund's adjuvant using multiple subcutaneous sites (5). The animals were boosted with the 0.25 mg immunogen in incomplete Freund's adjuvant at three-week intervals for a total of 4 additional immunizations.

The serum antibody titers to a BSA-conjugated version of the same peptide were monitored during the course of the immunization by standard ELISA methods. Animals (2) were chosen for splenectomy based on the titer data. Rabbit hybridomas were generated from spleen-derived lymphocytes fused with a rabbit fusion partner cells (Spieker-Polet, 1995 PNAS USA 92(20):9348-9352). Cell growth was examined 2-3 weeks after fusion in multiple plates.

Positive hybridomas were screened via ELISA on plates coated with the BSA-immunogen peptide conjugate. Multiple positive clones from each fusion were identified. Further screening involved binding to intact IgG1 and various enzymatically-generated F(ab')2 fragments of IgG1. From these screening and counter-screening tactics, three clones (designated 33-2, 91-2, and 68-6) were chosen based on strong selectivity of binding to the immunogen peptide and to F(ab')2 fragments with C-termini at or near the C-terminus of the immunogen peptide and with minimal binding to intact IgG1. The positive hybridomas were subcloned and expanded.

Rabbit IgG was purified from individual cell supernatants by standard methods including chromatography on immobilized protein A. The specificity of the purified rabbit IgGs for binding to peptide analogs of the human IgG1 hinge region, as well as intact IgG and purified IgG fragments created of single or doubly cleaved (F(ab')2) cleaved with mAbs using IdeS and MMP-3 enzymes were tested in standard ELISA protocols. Briefly, the peptides which were synthesized by standard peptide chemistry and were N-terminally biotinylated were captured on streptavidin-coated wells. The IgG and fragments were directly coated at 10 µg/mL. Binding of rabbit mAbs was detected by well-characterized goat anti-rabbit IgG Fc-horseradish peroxidase and OPD substrate systems.

Figure 11:
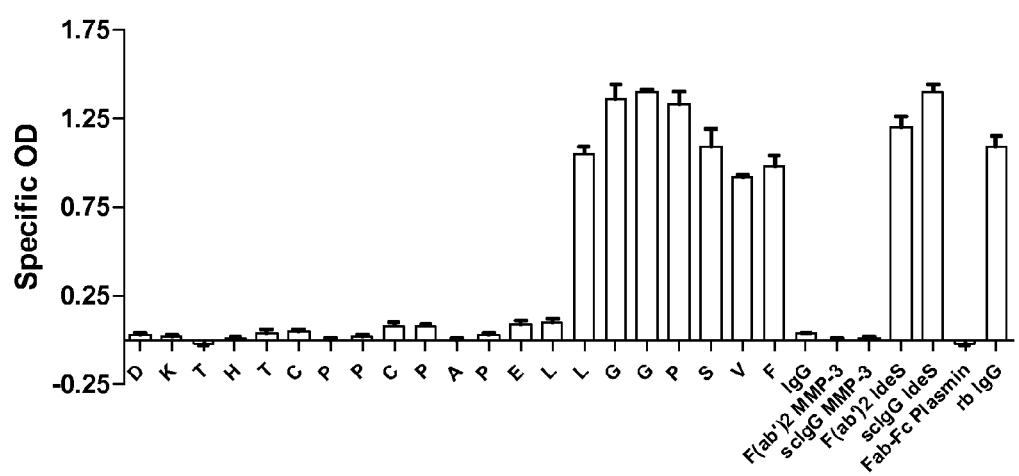
FIG. 11 shows the relative reactivity of rabbit monoclonal antibody targeting cleavage fragments from human IgG1 hinge as peptide analogs and to antibody fragments terminating at the residue specified (see FIG. 3).

The ELISA results for rabbit mAb 91-2 are shown in FIG. 11. There was a clear selectivity of binding for lower hinge peptides terminating at any of the residues 16-23 of SEQ ID NO: 1 (L-L-G-G-P-S-V-F). There is little or no binding to the peptides terminating at any of the upstream residues corresponding to those segments of the upper hinge, core hinge or early lower hinge encompassed by 3-15 of SEQ ID NO: 1 (D-K-T-H-T-C-P-P-C-P-A-P-E). There was negligible binding to the MMP-3 generated F(ab')2 fragment and scIgG fragment (in agreement with the lack of binding to the peptide analogs of the MMP-3 cleavage site between residues 14 and 15 of SEQ ID NO: 1 (ending in P-A-P). In contrast, there was substantial binding to the Ides-generated F(ab')2 fragment and scIgG which should have the C-terminal sequence (-P-A-P-E-L-L-G). Thus, the rabbit mAb binding specificity conformed well to the immunogen to which it was elicited. Directly coated rb (rabbit) IgG was a positive control.

Complement Assay

WIL2-S cells, a lymphoblastoid B-cell line expressing CD20 (ATCC CRL-8885), were used as target cells for CDC assays. 50 μl of cells were added to the wells of 96-well plates for a final concentration of $8 \times 10^4$ cells per well in RPMI, 5% heat-inactivated FBS, 0.1 mM nonessential amino acids, 1 mM sodium pyruvate, penicillin (500 U/ml), streptomycin (500 U/ml), 2 mM L-glutamine. An additional 50 μl was added to the wells with or without antibodies of various concentrations and the plates were incubated at room temperature for 2 hours. 50 μl of 10% rabbit complement (Invitrogen) was added to the wells and the plates were incubated for 20 minutes at 37° C. All samples were performed in triplicate. The plates were centrifuged at 200 g for 3 minutes and 50 μl of supernatant was removed to separate plates and CDC was measured with lactate dehydrogenase (LDH) cytotoxicity detection kit (Roche). Absorbance was measured using a Spectra max Plus 384 (PerkinElmer). Data were normalized to maximal cytotoxicity with Triton X-100 (Sigma Aldrich) and minimal control containing only cells and complement alone.

Figure 12:
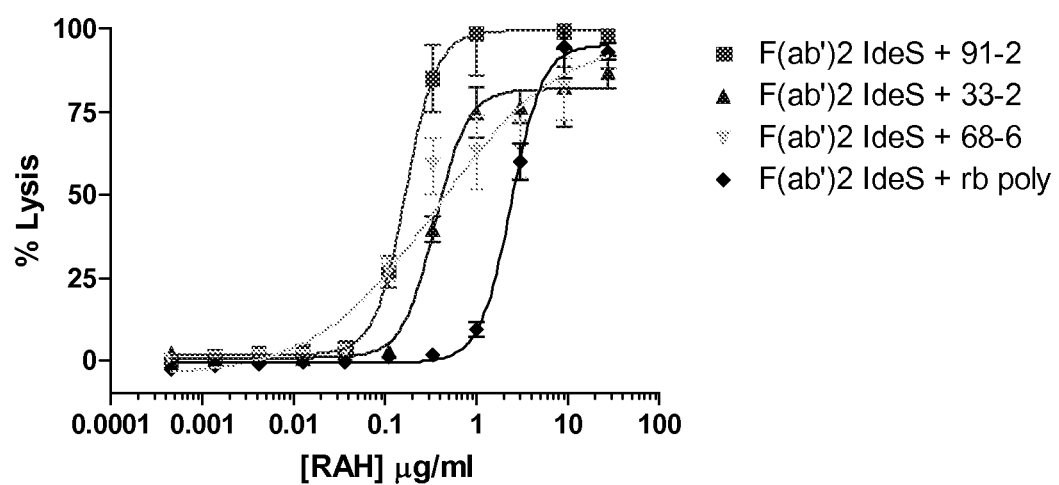
FIG. 12 shows the concentration dependence of three different rabbit monoclonal antibodies targeting cleavage fragments of human IgG1 hinge in restoring complement-dependent cell lysis (CDC) to F(ab')$_2$ created by digesting IgG1 with IdeS compared to a rabbit polyclonal prepared to cleavage peptide analogs (rb poly).

FIG. 12 shows that the 3 rabbit cleavage site specific mAbs were able to restore complement dependent cell lysis to the target cells when titrated in the presence of a fixed concentration of the F(ab')2 fragment of an antibody that binds CD20. The rabbit mAbs were more effective, and, at lower concentrations than a polyclonal rabbit cleavage site specific mAb preparation (a component of the same detection system for serum scIgG described earlier). Intact antibody to CD20 was active, as expected, but its F(ab')2 fragment and scIgG version were not active alone. The rabbit cleavage site specific mAbs were not able to direct cell lysis in the absence of cell-binding F(ab')2 fragment. These results establish that monoclonal cleavage site specific antibodies can reconstitute complement-mediated effector function to otherwise inactive proteolytic cleavage products of IgG1.

In order to test the restoration of effector functions in human system, the rabbit antibody variable domains of Mab 91-2 were cloned, fused to human constant domains and expressed in HEK293 cells. The resulting rabbit-chimeric Mab was designated 2095-2. The antibody specificity was again tested by binding to cleavage site peptides in an ELISA format and confirmed that the highest affinity was for the peptide terminating with -P-A-P-E-L-L-G.

The specificity of binding was further examined using a Fab fragment of the 2095-2 antibody using a surface plasmon resonance platform (Biacore). Briefly, the Fab was immobilized to a CM5 sensor chip in a Biacore 2000 at three different surface densities (8500, 1650, and 350 RU) using standard NHS/EDC coupling. The running buffer contained 10 mM HEPES pH 7.4, 150 mM NaCl, and 0.01% Tween-20. Data were collected at 25° C.

Three N-terminally biotinylated peptides were tested for binding of to the immobilized Fab: WT, representing the expected sequence of a peptide fragment from a human IgG1 cleavage site after cleavage by the *Streptococcus pyogenes* IdeS protease; E233A, representing a variant of having a single alanine substitution at the amino acid residue four positions upstream of the C-terminus; and L234A, a variant having a single alanine substitution at the amino acid residue three positions upstream from the C-terminus. The peptides were modified by substituting serine for cysteine to make them compatible with the coupling chemistry and preserve the monomeric structure.

Peptides Wild type and E233A were tested in a 3-fold dilution series using 588 nM and 2.9 uM as the highest concentration, respectively. Peptide L234A was tested at 14.7 uM as the highest concentration in a 2-fold dilution series. Each peptide concentration series was tested in triplicate over the three different density Fab surfaces. The association and dissociation were monitored for 1 minute. Surfaces were regenerated with a 12 second injection of 1/500 dilution of phosphoric acid. The response data from each surface were globally fit to determine the binding constants summarized in the table below. Each peptide interaction fit very well to a simple 1:1 (Langmuir) model.

The association rates ($k_a$ in M-1s-1)) varied by less than a factor of 10, however, the dissociation rates ($k_d$ in s-1) varied by more than 200-fold. The calculated $K_D$ in nM for the three peptides is shown below (Table 2).

TABLE 2

| Peptide | $k_a$ (M-1s-1) × $10^{-5}$ | $k_d$ (s − 1) | $K_D$ |
|---|---|---|---|
| Wt Biotin-TSPPSPAPELLG (SEQ ID NO: 13) | 5.22 ± 0.04 | 0.00443 ± 0.02 | 8.5 nM |
| E233A Biotin-TSPPSPAPALLG (SEQ ID NO: 14) | 7.29 ± 0.03 | 0.1070 ± 0.04 | 146.8 nM |
| L234A Biotin-TSPPSPAPEALG (SEQ ID NO: 15) | 1.24 ± 0.01 | 1.03 ± 0.01 | 8340 nM |

These results indicate that the monoclonal antibody 2095-2 is highly specific for the binding to the immunogen used which is an analogue of the IdeS cleavage site peptide from the N-terminal (upstream) sequence of human IgG1 and is in monomeric conformation due to the removal of cysteine residues.

Example 11

In Vivo Model for Cleavage Site Specific Antibody

In order to test the capacity of cleavage site specific antibodies to rescue cleaved IgGs in vivo, a model for bacterial infection employing a "tissue cage" (Fernandez J A, et. al. (1997) *Antimicrob. Agents Chemother.* 43(3):667-671) was adopted. In this system, a wiffle ball is surgically implanted subcutaneously in the dorsal cervical area. The model allows the infectious agents to be localized within an easily accessible fluid compartment, a tissue pouch, and has been used to assess the efficacy of antibiotics against bacteria.

In the present system, the rabbit wiffle fluid ball was found to contain approximately 1.5 mg/ml IgGs, in contrast to 5-10 mg/ml of IgGs reported in rabbit serum. Our hypothesis is that infection of rabbits with the GluV8-expressing bacteria *S. aureus* would result in cleavage of the rabbit IgGs within the wiffle ball. Furthermore, vaccination of rabbits with a GluV8-cleaved IgG cleavage site specific peptide analogue would result in robust cleavage site specific titers that would provide a measure of protection against *S. aureus*.

In order for the model to provide a positive result in demonstrating that rabbit cleavage site specific antibodies can provide some level of protection against *S. aureus* infection, four factors must be operating. First, GluV8 must be capable of cleaving rabbit IgGs. Second, rabbits must have either some pre-existing immune reactivity to *S. aureus* antigens or they must be able to generate an antibody-mediated immune response against *S. aureus* shortly after infection as these will become the subject IgG. Third, the vaccination approach must yield cleavage site specific antibodies of sufficient affinity and specificity to bind the cleaved rabbit IgGs. Finally, animals immunized with the cleaved antibody analogues must demonstrate a measurably different response than non-immunized animals.

We previously showed that GluV8 cleaves human IgG1 between the amino acids E233 and L234 (WO2009/023457A1, Ryan M H, et al. (2008) *Mol Immunol* 45(7): 1837-1846) located in lower hinge region in vitro. The sequence of the rabbit IgG lower hinge region in this region is identical to the human IgG1 sequence except for the single amino acid change, A231P. As the GluV8 cleavage site it was expected that the enzyme would act on rabbit IgG.

| | |
|---|---|
| Human IgG1 | $_{229}$CPAPELLGG$_{236}$ |
| Rabbit IgG1 | $_{229}$CPPPELLGG$_{236}$ |

Rabbit IgGs from the serum and from the *S. aureus* containing wiffle ball fluid of rabbits three days after inoculation were purified separately using a Protein A reagent. The resulting preparations of rabbit IgGs were analyzed by MALDI to determine the amount of IgG cleavage. The MALDI analysis of the rabbit serum IgGs revealed three primary peaks, corresponding to the singly-charged molecular ion of intact IgG (143,600 Da), the doubly-charged molecular ion of intact IgG (71,700 Da), and rabbit albumin (65,800 Da). In contrast, the MADLI analysis of wiffle ball rabbit IgGs contained the singly-charged molecular ion of an Fc fragment (52,800 Da), the doubly-charged molecular ion of an Fc fragment (25,500 Da), and a small peak corresponding to the singly-charged molecular ion of intact IgG (143,700 Da). These results indicated that rabbit IgGs purified from *S. aureus* containing wiffle ball fluid contained cleaved IgGs, whereas rabbit IgGs purified from the serum contained intact IgGs with no detectable IgG cleavage products. Therefore, we concluded that rabbit IgGs in vivo, like human IgG1 in vitro, are susceptible to cleavage within a microenvironment containing *S. aureus*.

With regard to the immune status of the study animals toward *Staph. aureus*, the presence of pre-existing immune reactivity in serum was tested by ELISA using two *S. aureus*-derived antigens. These were *Staph*. alpha toxin (alpha-hemolysin, H1a) and Staphylococcal Enterotoxin B (a toxin commonly associated with food poisoning). The pre-study serum from the six rabbits that subsequently were immunized with the hinge analogue peptide, and the pre-inoculation serum from 6 non-immunized control rabbits were tested at 1:50, 1:200 and 1:800 dilutions for binding to the two toxins. A positive titer was quantified as the highest dilution at which optical density (490 nm) was two-fold or greater than the signal obtained in the corresponding control well (non-antigen coated). In addition, a human integrin and chicken egg albumin were tested as potential negative controls since it was unlikely that rabbits would have been exposed to such proteins. The results are tabulated below (Table 3).

TABLE 3

| Antigen | Incidence of positive reactivity | Titers (n) |
|---|---|---|
| Staph alpha toxin | 8/12 | 1:50 (2), 1:200 (1), >1:800 (5) |
| Staph enterotoxin B | 12/12 | 1:50 (3), 1:200 (3), >1:800 (6) |
| Human integrin | 1/12 | 1:50 (1) |
| Chicken egg albumn (ovalbumin) | 4/12 | 1:50 (4) |

Results

The results indicated that there was a substantial incidence of anti-Staphylococcal toxin reactivity in the 12 study animals. In some rabbits, the titers would clearly have exceeded the maximum dilution tested (1:800). In contrast, the incidence of immune reactivity to the human and chicken antigens was markedly lower and was detectable only at the 1:50 dilution. These results supported the supposition that rabbits are naturally exposed to *S. aureus* in their lifetimes and should be capable of immediate targeting of *S.* antigens upon inoculation, or possess the ability to rapidly mount a recall response. These findings suggest that a spectrum of antibodies to *Staph. aureus* antigens may be present including antibodies to cell surface components.

Example 12

Immunization

The procedure described in Example 11 verified that test subject rabbits have had previously developed immune titers to *Staph. aureus* antigens which would provide for natural bacterial targeting antibodies. To determine if rabbits would generate a sufficiently specific and robust cleavage site specific antibody response after vaccination with cleavage site peptides to protect against a bacterial challenge, the following experiment was performed where rabbits were immunized with a GluV8-cleavage site peptide analogue (residues 7-15 of SEQ ID NO: 1, TCPPCPAPE) conjugated to the immunogen KLH.

A peptide analogue of residues 225-233 of the human IgG1 hinge was chemically synthesized. The immunogen peptide, C-T-S-P-P-S-P-S-P-A-P-E (Cys-Thr-Ser-Pro-Pro-Ser-Pro-Ala-Pro-Glu, SEQ ID NO: 16) was designed which included an N-terminal Cys for linkage and an internal substitution of Ser for the Cys that occurs at position 226 and 229 in the IgG to avoid oxidation and dimerization of peptides at those positions.

The peptide was prepared on an ABI 433A Peptide Synthesizer using 0.25 mmol scale FastMoc chemistry and Fmoc-Glu(OtBu)-Wang Resin. Approximately 190 mg of crude peptide was released from the resin and was purified via multiple injections onto two Vydac C-18 columns. Fractions were collected and analyzed by RP-HPLC and MALDI-TOF MS. Pooled fractions yielded 38 mg of lyophilized product having free cysteine by Elllman's test.

The conjugation of the peptide to keyhole limpet hemocyanin (KLH) was accomplished with EDC coupling chemistry (1-Ethyl-3-[3-dimethylaminopropul]carbodiimide) using the Imject Immunogen EDC Kit (Pierce product no. 77622). 22 mg of purified peptide at 4 mg/mL in EDC conjugation buffer was combined with an equivalent mass of KLH at 10 mg/mL in water. Linkage of peptide to KLH occurred following addition of EDC solution to the mixture with gentle mixing for 2 hours at room temperature. All of the above steps were performed according to the manufacturer's directions. The conjugation mixture was dialyzed against PBS to remove excess linkage reagents. The KLH-peptide conjugation was confirmed by sandwich immunoassay using the polyclonal rabbit cleavage site specific specific antibody preparation RAH (reactive to a cleavage site specific analogue peptide ending with the sequence C-P-P-C-P-A-P-E) as described in Example 3 and biotinylated anti-KLH antibody as capture and detection antibodies, respectively.

Following immunization, the reactivity of rabbit serum to the peptide analogue was tested by ELISA. Table 4 shows the titers (as the reciprocal of the dilution at which a signal was detectable), which indicate that all of the rabbits had antibodies reactive to the cleavage site specific analogue peptide detectable in the serum. One animal (657) had a very low level of detectable antibodies to the immunogen with a 1/titer equaling 640. Cleavage site specific antibodies were also detected in the wiffle ball fluids of all six rabbits, with the same animal (657) having a low level of detectable antibodies. Therefore, five of the six rabbits demonstrated robust cleavage site specific antibody titers detectable in both the serum and wiffle ball fluids.

TABLE 4

| Rabbit | Serum (titer) | Wiffle ball (titer) |
|---|---|---|
| 651 | 12,800 | 3,200 |
| 653 | 51,000 | 12,800 |
| 656 | 820,000 | 51,000 |
| 657 | 640 | 320 |
| 659 | 51,000 | 12,800 |
| 661 | 205,000 | 12,800 |

In the final phase of the study, the immunized and non-immunized rabbits were inoculated with 6.2 log 10 colony forming units (CFUs) of *S. aureus* (ATCC 29213) directly into the wiffle-ball compartments.

Figure 13:
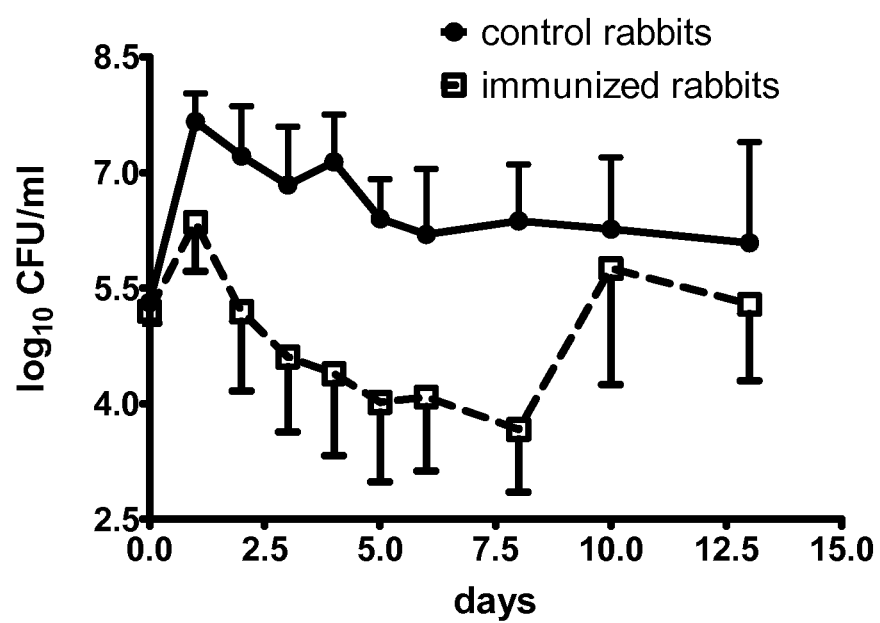
FIG. 13 shows the mean log colony bacterial count and SEM in the whiffle ball after inoculation with *Staph. aureaus* of control rabbits (black line) vs. immunized rabbits (dashed line).

The bacterial counts and test subject viability were monitored over the course of two weeks for bacterial counts and survival. The data shown in FIG. 13 indicate that during the first week of the study, the average bacterial counts for control animals were several logs higher than cleavage site specific vaccinated animals. For example, on day 2 the control had 7.2 $\log_{10}$ CFU/ml wiffle ball fluid while the immunized group had 5.2 $\log_{10}$ CFU/ml wiffle ball fluid.

Figure 14:
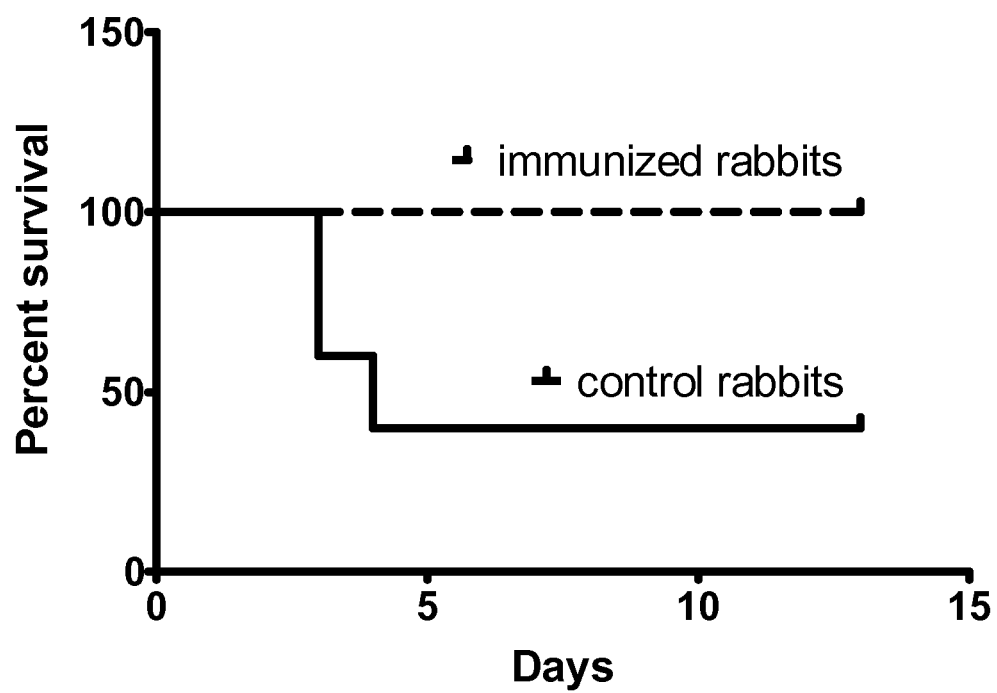
FIG. 14 is Kaplan Meier survival plot for rabbits inoculated with *Staph. aureaus* showing the control rabbits (black line) and immunized rabbits (dashed line).

The differences in bacterial counts translated into a profound difference in rabbit viability. By the end of the two week study, only 40% percent of the control animals survived, while 100% of the cleavage site specific vaccinated animals were viable (FIG. 14).

Therefore, these results supported the hypothesis that innate immunity to pathogens, when present, can be restored to an effective level by the present method of immunization against the byproduct of pathogen produced proteases, presumably the cleaved but still immunoreactive anti-*Staph. aureus* IgG. This process was evidenced by not only reducing bacterial counts of inoculated animals with a highly proteolytic bacterium, but also by the fact that the animals were rescued from mortality.

Example 13

Passive Immunization to Treat Cancer

To demonstrate the principle of restoration of effector functions by an cleavage site specific antibody to a tumor targeting Mab, a murine human tumor xenograft model, the MDA MB 231 orthotopic xenograft model in SCID Beige mice, was used with an antibody called CNTO860 (U.S. Pat. No. 7,605,235), directed against human tissue factor (CD142) previously demonstrated to show the ability to reduce tumor growth in the model.

The study was designed to show that proteolytic cleavage of the lower hinge domain of the IgG1 of CNTO860 would render the antibody ineffective and evaluate if an cleavage site specific cleavage site mAb would restore the anti-tumor efficacy of cleaved CNTO860 in the MDA-MB-231 orthotopic xenograft model in SCID Beige mice.

The intact anti-tumor antigen antibody, CNTO 860, comprises a human IgG1 constant regions. A protease cleaved antibody, CNTO860, was prepared using the bacterial protease IdeS, as described above.

The antibody preparations were diluted fresh each week and supplied at 10 μg/mL in PBS for animal dosing at 0.1 mg/kg. The mAb 2095-2 (chimeric cleavage site specific cleavage$_{IdeS}$) was administered alone at same schedule as for the 860 variants above at 1.0 mg/kg.

Immunocompromised mice (SCID Beige mice (C.B-17/IcrCrl-scid-bgBR) approximately 18-20 g in weight obtained from Charles River Laboratories) were anesthetized and implanted with MDA-MB-231 a human breast carcinoma line (ATCC #HTB-26) cells suspended at $5 \times 10^7$ cells/mL in serum-free DMEM into the (Right axillary number 2 or 3) mammary fat pad in a volume of 50 μL as specified by an IACUC approved protocol.

Mice, eight per group, received test substances or PBS (control group) as shown in the Table 5 (below). Group 4 received CNTO 860 single cleaved IgG dosed as specified above for mono-therapy plus mAb 2095-2 administered at 1.0 mg/kg, dosed with a 2-hr delay i.p. The dosing began on day 3 of the study and was repeated once per week.

TABLE 5

| Group | First Injection (i.v., 0.2 cc/20 g) | Dosage | Second Injection (i.p.) | Dosage |
|---|---|---|---|---|
| 1 | PBS-- | — | — | |
| 2 | CNTO860 | 0.1 mg/kg | — | |
| 3 | CNTO860 single cleaved IgG | 0.1 mg/kg | — | |
| 4 | CNTO860 single cleaved IgG | 0.1 mg/kg | Cleavage site specific mAb 2095-2 | 1 mg/kg |
| 5 | PBS | — | Cleavage site specific mAb 2095-2 | 1 mg/kg |

The study was terminated when the control group tumors reach 800 mm3 in volume. At termination, whole blood was collected via cardiac puncture into prepared EDTA coated tubes from all animals. At the termination of the study, body weights and tumor measurements were recorded and the primary tumors surgically removed, and weighed.

Results

Figure 15:
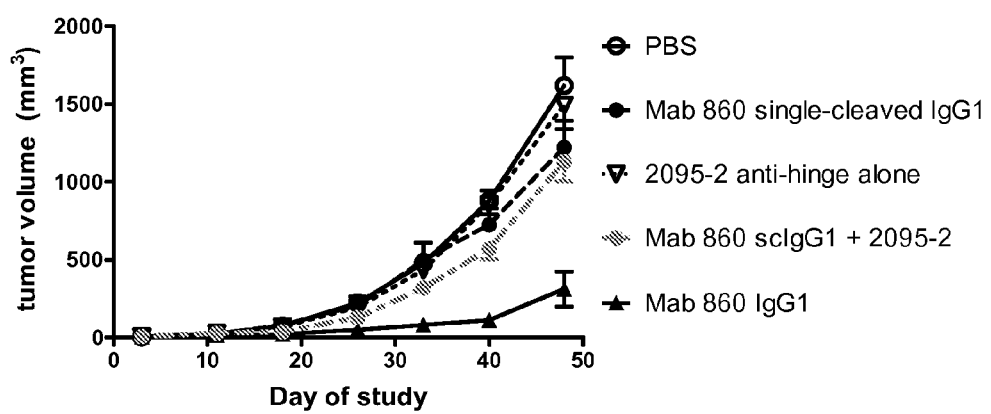
FIG. 15 shows the change in tumor volume over time for five groups of mice implanted with human breast carcinoma cells (MDA-MB231) and treated with either a tumor targeted Mab (860) alone (solid triangles); a protease treated preparation of 860, 860 scIgG (closed circles); the cleavage site specific antibody preparation 2095-2; the 860 scIgG plus the cleavage site specific antibody preparation 2095-2; or PBS (open circles).

The mean tumor volumes for each group of mice at specific times during the experiment are shown in FIG. 15. Statistically, the tumor volumes in the CNTO860 treated group were lower compared to each of the other groups starting at Study Day 11. The tumor volumes in the combination CNTO860 plus mAb2095-2 group were lower than those in the PBS group from Study Days 18-40; lower than those in the CNTO860 scIgG alone group from Study Days 26-40; and lower than those in the mAb2095-2 alone group from Study Days 18-40. There were no other differences in tumor volume among the treatment groups.

The CNTO860 alone group had much smaller final tumor weights than every other group. Additionally, the combination CNTO860 plus mAb2095-2 group had smaller tumors than both the PBS and mAb2095-2 alone groups. There were no other differences among the treatment groups in tumor weight.

These results demonstrate that passive immunization with a cleavage site specific antibody preparation restores anti-tumor activity where a cleaved target specific antibody in present.

Example 14

Target Cell Depletion Using a Cleavage Site Specific Antibody and Cleaved Targeting Antibody In the following experiment, the in vivo administration of a cleavage site specific antibody (rabbit-human chimeric mAb 2095-2 with specificity to human IgG1 cleaved by IdeS (chimeric cleavage site specific cleavage$_{IdeS}$)) following administration of a single-cleaved IgG or double-cleaved IgG, (a F(ab')$_2$), was investigated.

The anti-platelet integrin ($\alpha_{IIb}\beta_{IIIa}$, also called IIb/IIIa) binding antibody, c7E3, was used as the targeting antibody for several reasons. The anti-platelet mAb was a human IgG1 chimeric that was shown in a pilot study to result in profound platelet clearance after 24 hours with recovery over 5 days (indicating substantial acute recognition of the mAb by the canine Fcγ receptors and/or complement system). Additionally, the effect was distinguishable at a dose of the intact IgG (0.05 mg/kg) that did not cause inhibition of platelet function and therefore not likely to cause clinically relevant bleeding complications. Lastly, circulating platelet numbers provide a readily quantifiable endpoint and the multiple blood samplings in this non-terminal study did not pose blood loss artifacts or risks for animals of this size.

Materials and Methods

Three preparations of c7E3 were used: the intact murine-human IgG1 chimeric antibody, a single cleaved and a F(ab')$_2$ prepared using the bacterial enzyme IdeS.

First, the c7E3 antibody antigen binding and platelet depletion parameters were established in dogs. The results of the test infusions of showed that 0.01 mg/kg dose (that would be calculated to be more than sufficient to drive platelet clearance in humans) was ineffective in dogs at 2 and 24 hours and was indistinguishable from the saline group. The 0.05 mg/kg dose had little effect by 2 hours but at 24 hours had resulted in >90% platelet clearance. The 0.2 mg/kg dose of c7E3 IgG resulted in profound platelet clearance at 2 hours that was then maintained at 24 hours. These results provided the needed information to assign the minimum dose in dogs (0.05 mg/kg) that would result in substantial, acute platelet clearance (24 hours).

Effect on Platelet Function c7E3 inhibits platelet aggregation by binding to platelet surface IIb/III3 receptors—thereby blocking the ability of fibrinogen to bind to the receptors on activated platelets and to clump them together. The respective inhibitory profiles of intact and single-cleaved c7E3 IgG were tested in a platelet aggregation assay. Platelet aggregation is measured as an increase of light transmission through a platelet suspension after activation with a physiological agonist. The inhibition is compared to control aggregation to 5 µM adenosine diphosphate (ADP). The percent inhibition was calculated as: control aggregation—test aggregation×100%, divided by control aggregation.

The results indicated that there was no loss of binding/inhibition of c7E3 to platelets after single lower hinge cleavage by the IdeS protease.

c7E3 IgG and c7E3 IgG single-cleaved by IdeS protease were also compared in vivo. Three groups of 5 animals received either saline control, intact c7E3 IgG (0.05 mg/kg) or c7E3 single-cleaved IgG (0.05 mg/kg). Platelet counts were monitored at baseline and at 2, 24, 48, 72 and 96 hours post-administration. Limiting the study to 5 days minimized the likelihood of anti-c7E3 immune responses that might confound the interpretation of the results. The results are presented in FIG. 3 as the mean platelet count±SD for each animal group at each time point. The extent of the error bars connotes the normal variability of platelet counts in different animals (for example, the predose counts for the 5 animals in the single-cleaved IgG treatment group were 175,000, 355,000, 305,000, 276,000 and 334,000 per µL, respectively). Nevertheless, the mean results clearly confirmed that intact c7E3 IgG induced a substantial decrease of platelet numbers with a nadir apparent at 24 hours. The single cleaved version of c7E3 IgG at the same 0.05 mg/kg dose was essentially without effect. The single-cleaved c7E3 and saline control groups showed similar profiles throughout the 96-hour monitoring period. The platelet count declines at the final 96-hour determination in both the saline control group and single-cleaved c7E3 group suggested a non-immune-mediated cause (e.g. blood volume losses from the repeated sampling).

Platelet counts in the intact c7E3 IgG group showed a gradual recovery reaching approximately 50% of the pre-dose level by 96 hours. No adverse clinical findings (e.g. bleeding) were noted in any group and this is consistent with the known human tolerance for limited periods of low circulating platelet counts and/or profound inhibition of platelets.

The finding in this study was that single proteolytic cleavage of IgG in the lower hinge results in profound loss of effector function. Despite its equivalent binding to platelets, the single cleaved derivative of c7E3 was unable to engage the components of the immune system that normally remove opsonized cells (as seen with intact c7E3 in this study). These in vivo results confirmed similar in vitro findings with several cell-targeting mAbs whose single-cleaved derivatives essentially lose all effector functions in ADCC and complement assays.

To be consistent with the prior experiments, the variants of c7E3 were all administered at the 0.05 mg/kg dose. The study protocol included 7 different groups of 3 animals as listed in Table 6. The unique aspect of the experiment (groups 6 and 7) involves the infusion of the first targeting mAb followed by the cleavage site specific mAb after a 10 minute delay. The cleavage site specific IdeS cleavage site mAb, 2095-2, was administered at 0.5 mg/kg; 10-fold higher than the dose used for all of the c7E3 variants. The higher dose was chosen in order to maximize the complexation of cleavage site specific mAb with platelet-bound c7E3 variants. All mAbs were delivered by slow infusion over a 20 minute period. Platelet counts were monitored over a 96-hour period. The platelet counts were normalized to the pre-dose count within each animal for clarity of presentation and to minimize the normal variability in numerical platelet counts in these small 3-animal groups.

TABLE 6

Study protocol for restoration of function study in dogs.

| Group | Test article(s) | Duration of 1st infusion | Delay | Duration of 2nd infusion | Blood collection times (H after start) |
|---|---|---|---|---|---|
| 1 | Normal saline for injection | 20 min | NA | NA | Predose, 2, 24, 48, 72, 96 |
| 2 | c7E3 IgG @ 0.05 mg/kg | 20 min | NA | NA | Predose, 2, 24, 48, 72, 96 |
| 3 | c7E3 F(ab')$_2$ @ 0.05 mg/kg | 20 min | NA | NA | Predose, 2, 24, 48, 72, 96 |
| 4 | c7E3 sc IgG @ 0.05 mg/kg | 20 min | NA | NA | Predose, 2, 24, 48, 72, 96 |
| 5 | mAb 2095-2 @ 0.5 mg/mg | 20 min | NA | NA | Predose, 2, 24, 48, 72, 96 |
| 6 | c7E3 F(ab')$_2$ @ 0.05 mg/kg + mAb 2095-2 @ 0.5 mg/mg | 20 min | 10 min | 20 min | Predose, 2, 24, 48, 72, 96 |
| 7 | c7E3 sc IgG @ 0.05 mg/kg + mAb 2095-2 @ 0.5 mg/mg | 20 min | 10 min | 20 min | Predose, 2, 24, 48, 72, 96 |

Figure 16:
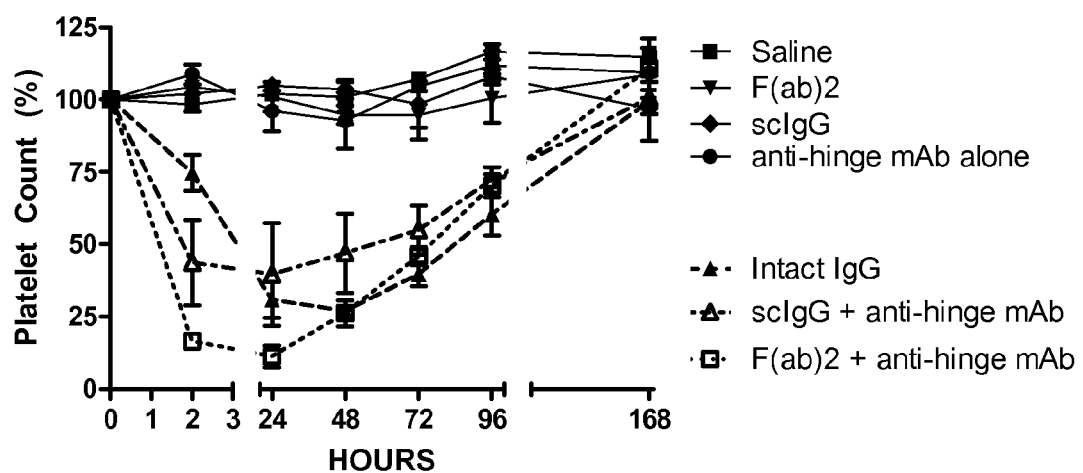
FIG. 16 shows the effect on circulating platelet numbers of an anti-platelet integrin Mab (c7E3) or proteolytic cleavage products of the Mab, administered alone and in combination with anti-cleavage site mAb, 2095-2, on platelet counts in dogs, where each point represents the mean±SD of the determinations of three animals.

The results are presented in FIG. 16. A number of findings emerged from this study. As the dose finding studies show, intact c7E3 IgG administered at 0.05 mg/kg, induced substantial platelet clearance with a nadir apparent at 24-48 hours. Recovery of platelet numbers began at approximately 72 hours and slowly increased through the 96-hour determination. An additional blood sample was incorporated into the study at 7 days (168 hours) to allow an assessment if full recovery would occur. Full recovery did occur in all applicable treatment groups by 7 days.

In contrast to intact c7E3 IgG, single-cleaved IgG and F(ab')$_2$ were without effect on platelet numbers and the platelet number changes in these groups was not different from the saline control group. Likewise the cleavage site specific mAb, 2095-2, when infused alone (group 5) had no measurable impact on circulating platelets. However, in the c7E3 F(ab')$_2$ plus mAb 2095-2 group, there occurred a rapid decrease of the platelet count such that at 2 hours the effect was nearly maximal. In addition, the extent of the platelet decline appeared to be greater in the groups where the cleavage site specific antibody was administered after the cleaved antibody fractions than in the group receiving intact c7E3 IgG (alone; group 2) at the 2 and 24 hour determinations. Thereafter, platelet counts gradually recovered and by 48 hours the rate of recovery paralleled that in the intact c7E3 IgG group.

In the F(ab')$_2$ combination group, when mAb 2095-2 was coupled with single-cleaved c7E3 IgG the extent of platelet clearance was not as marked as seen in the F(ab')$_2$ group and may be attributable to one poorly responsive animal in the scIgG group (also reflected in the wide error bars for this group). Nevertheless, platelet clearance occurred more quickly than had been evident in the intact c7E3 IgG group. The scIgG result is important since the targeting of this derivative with the mAb in vivo appears to have been as effective as the targeting of F(ab')$_2$—an outcome that was not predictable based on in vitro findings.

Discussion/Conclusions

The series of animal studies described here confirmed earlier in vitro findings that single-cleaved proteolytic derivatives of IgGs lose the ability to remove cells to which they are bound—in this case in vivo. The intact c7E3 IgG was shown to induce platelet clearance within 24 hours in the dog at doses ≧0.05 mg/kg. The 0.05 mg/kg dose was calculated to be sufficient to provide several thousand copies of IgG per platelet or about 5% $\alpha_{IIb}\beta_3$ receptor blockade. A substantially higher level of receptor blockade is known to be required for inhibition of platelet function (about 80,000 copies per platelet). Thus, the canine immune system has the capacity to clear cells that are opsonized with IgG at this fractional level.

The results showed that a single proteolytic cleavage of the human IgG1 lower hinge abrogated the platelet clearance properties of the c7E3 IgG. Here, the functionally-inactive, single-cleaved IgG was prepared ex vivo by partial digestion with IdeS protease, however, and as demonstrated herein, other proteases yield IgGs with similar loss of function. The single IdeS cleavage did not impact the antigen binding characteristics of c7E3 as shown in an in vitro platelet inhibition assay. The findings suggested a mechanism to explain certain shortcomings of host immune systems in pathologies associated with hostile proteolytic environments (e.g. certain tumors, bacterial infections, inflammatory settings).

The study findings pointed to a means to correct the proteolytic defect in IgGs. Namely, a specific mAb vs. the site of proteolytic cleavage should deposit a functional Fc domain on the inactive cell-bound antibody and thereby restore Fc-mediated effector functions.

A monoclonal antibody to the IdeS cleavage site in the IgG hinge was generated by immunization of rabbits. This mAb, 2095-2, after modification to incorporate human constant regions, readily restored in vitro cell killing to inactive F(ab')$_2$ or single-cleaved IgGs in ADCC and complement assays.

The key test was to employ 2095-2 in combination with IdeS-generated proteolytic derivatives of c7E3 IgG in vivo. The 2-stage protocol was designed to allow c7E3 to first bind to platelets and to then follow with an excess of the cleavage site specific mAb to complex with the platelet bound c7E3s. In the presence of coupled anti-cleaved hinge Mab and a cleaved Mab, platelet clearance was more rapid and the degree of acute platelet clearance more profound (with c7E3 F(ab')$_2$) than was induced with intact c7E3 IgG alone. The rapidity of platelet clearance with the combined therapies is suggestive of an enhanced mode of immune cell killing/removal.

Example 15

Cleavage Site Specific Vaccination to Treat Cancer

The use of a hinge analogue peptide vaccination has potential to treat chronic human diseases such as invasive and metastatic cancer. Several invasive cancer animal models currently exist which are suitable for testing the efficacy of cleavage site specific directed vaccination as a means to treat invasive cancer.

The vaccination approach would confer a markedly different pharmacodynamic profile compared to anti-tumor mAb therapy alone. In the latter, an established tumor is subjected to an abrupt dosage of a monoclonal antibody to a specific target on its surface. The tumor may, or may not, already be targeted by host antibodies to the same antigen, or to additional antigens, on those cells. The vaccination strategy, if initiated early, would provide a continuous and comparatively invariant level of cleavage site specific host antibodies to engage any tumor-surface cleaved antibodies present at the sites of tumor growth or invasion as generated.

As demonstrated by using the innate humoral response of the rabbit in the previously described infection model, the cellular target of the primary response is almost immaterial; the secondary antibody wave restores effector function to any damaged primary antibody that is present. The inactivated and cell-bound-bound host antibodies would provide a variety of antigenic targets (and surface locations) for cleavage site specific Abs.

As demonstrated herein, a single- or double-cleaved antibody directed to and engaged with a cell surface antigen can be targeted by a cleavage site-specific antibody, thereby restoring the host ability to eliminate the target cell using effector functions provided by the intact cleavage site specific antibody. Another and markedly different approach would be to immunize the host against the sites of cleavage damage induced by proteases associated with specific diseases such as metastatic cancer. For example, tumor cells elaborate matrix metalloproteases that cleave IgG in the hinge. Vaccination against the sites of cleavage could provide host antibodies that would combat the molecular defects and augment immune function in that local environment.

The target of the damaged mAb(s) could be specific or could be multiply-targeted using a mixture of cleavage site specific peptides in order to protect against the action of multiple proteolytic enzymes without the need for detailed identification.

Thus, in accordance with the invention, a subject cancer patient in need of treatment, is vaccinated with a cleavage site peptide immunogen to generate a cleavage site specific antibody response either before, after or concurrent with treatment within a cancer treating antibody composition. In one instance, the immunogen is a MMP-3 or MMP-12 cleavage site peptide having the sequence terminating in the amino acid sequence P-C-P-A-P which is residues 10 to 14 of SEQ ID NO: 1.

What is claimed is:

1. An isolated human IgG protease cleavage site peptide consisting of an amino acid sequence of SEQ ID NO: 16.

2. The peptide of claim 1 conjugated to a carrier protein in a manner such that the C-terminus of the peptide is chemically bound to a carrier protein.

3. The peptide conjugate of claim 2, wherein the carrier protein is selected from the group consisting of keyhole limpet hemocyanin (KLH) or serum albumin.

4. A vaccine composition comprising the human IgG cleavage site peptide of claim 1 in association with one or more pharmaceutically acceptable carriers or adjuvants.

5. The vaccine composition of claim 4 where the adjuvant is selected from the group consisting of alum, incomplete Freund's adjuvant, complete Freund's adjuvant or MF59.

* * * * *